US009314514B2

(12) United States Patent
Eisele

(10) Patent No.: US 9,314,514 B2
(45) Date of Patent: Apr. 19, 2016

(54) MODIFIED NEUROTOXINS WITH POLY-GLYCINE AND USES THEREOF

(71) Applicant: MERZ PHARMA GmbH & CO. KGaA, Frankfurt am Main (DE)

(72) Inventor: Karl-Heinz Eisele, Frankfurt am Main (DE)

(73) Assignee: MERZ PHARMA GmbH & CO. KGaA, Frankfurt am Main (DE)

( * ) Notice: Subject to any disclaimer, the term of this patent is extended or adjusted under 35 U.S.C. 154(b) by 0 days.

(21) Appl. No.: 14/356,210

(22) PCT Filed: Nov. 8, 2012

(86) PCT No.: PCT/EP2012/072154
§ 371 (c)(1),
(2) Date: May 5, 2014

(87) PCT Pub. No.: WO2013/068472
PCT Pub. Date: May 16, 2013

(65) Prior Publication Data

US 2014/0308266 A1 Oct. 16, 2014

Related U.S. Application Data

(60) Provisional application No. 61/628,934, filed on Nov. 9, 2011.

(30) Foreign Application Priority Data

Nov. 9, 2011 (EP) .................................... 11188379

(51) Int. Cl.

| | |
|---|---|
| ***C07K 14/33*** | (2006.01) |
| ***A61K 38/48*** | (2006.01) |
| ***C12N 9/52*** | (2006.01) |
| ***C12N 15/62*** | (2006.01) |
| ***A61K 35/56*** | (2015.01) |

(52) U.S. Cl.
CPC ............ *A61K 38/4893* (2013.01); *A61K 35/56* (2013.01); *C07K 14/33* (2013.01); *C12N 9/52* (2013.01); *C12N 15/62* (2013.01); *C07K 2319/00* (2013.01)

(58) Field of Classification Search
None
See application file for complete search history.

(56) References Cited

U.S. PATENT DOCUMENTS 8,241,623 B1 * 8/2012 Bermudes .................... 424/93.4

FOREIGN PATENT DOCUMENTS

WO WO 2008/082889 A2 * 7/2008 ............. A61K 39/08

OTHER PUBLICATIONS

Swierzewski (Dystonia Follow Up, Prognosis, Prevention by (Aug. 24, 2007) downloaded from http://www.healthcommunities.com/dystonia/followup.shtml on Jun. 14, 2014).*
Beck Z. et al.: "Membrane-specific antibodies induced by liposomes can simultaneously bind to HIV-1 protein, peptide, membrane epitopes", Journal of Grug Targeting vol. 16, No. 7-8, pp. 535-542.
Dressler et al. (Dressler 2005, Mov Disord vol. 20 No. 12, p. 1617-1619.
Fischer 2007, PNAS vol. 104, No. 25, p. 10447-10452.
International Search Report for PCT/EP2012/072154 of Jan. 16, 2013.
Jost 2007, Drugs vol. 67, No. 5, p. 669-683.
Kanli Jiang et al: "[Alpha] genetic fusion construct between the tetanus toxin C fragment and the lysomal acid hydrolase [beta]-glucoronidase expresses a bifunctional protein with enhanced secretion and neuronal uptake", Journal of Neurochemistry, vol. 93, No. 5, Jun. 1, 2005, pp. 1334-1344.
Keller 2006, Neuroscience vol. 139, p. 629-637.
Krieglstein 1990, Eur J Biochem vol. 188, p. 39.
Krieglstein 1991, Eur J Biochem vol. 202, PF. 41-51.
Krieglstein 1994, J Protein Chem vol. 13, No. 1, p. 49-57.
Pearce 1994, Toxicol Appl Pharmacol vol. 128: 69-77.

* cited by examiner

*Primary Examiner* — Marcela M Cordero Garcia
*Assistant Examiner* — Mindy Newman
(74) *Attorney, Agent, or Firm* — Hueschen and Sage

(57) ABSTRACT

The present invention is concerned with modified neurotoxins. Specifically, it relates to a modified biologically active neurotoxin polypeptide comprising at least one poly-Glycine domain. Also contemplated is a polynucleotide encoding the modified neurotoxin polypeptide having a poly-Glycine domain fused to the N-terminus, to the C-terminus or to both of the heavy and/or light chain of the mature neurotoxin polypeptide, vector comprising it and a host cell comprising such a polynucleotide or a vector. Moreover, envisaged are the aforementioned compounds for use as a medicament for treating various diseases.

12 Claims, 2 Drawing Sheets

Fig. 2

Figure 1:
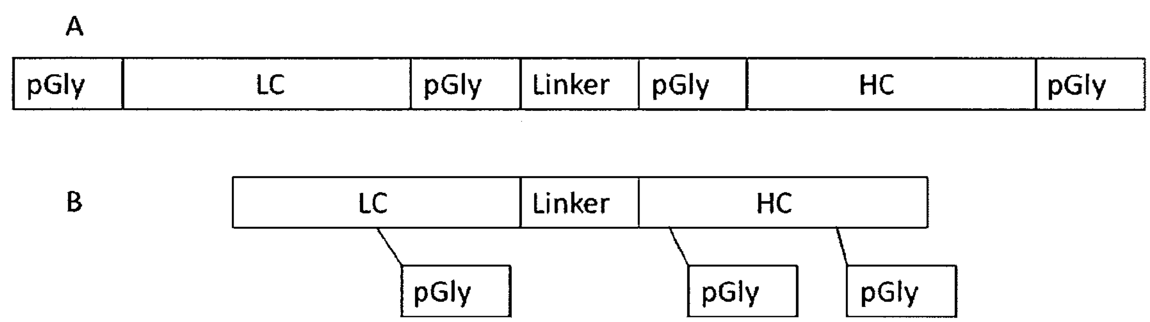

MPFVNKQFNYKDPVNGVDIAYIKIPNAGQMQPVKAFKIHNKIWVIPERDTFTNPEEGDLNPP
PEAKQVPVSYYDSTYLSTDNEKDNYLKGVTKLFERIYSTDLGRMLLTSIVRGIPFWGGSTID
TELKVIDTNCINVIQPDGSYRSEELNLVIIGPSADIIQFECKSFGHEVLNLTRNGYGSTQYI
RFSPDFTFGFEESLEVDTNPLLGAGKFATDPAVTLAHQLIYAGHRLYGIAINPNRVFKVNTN
AYYEMSGLEVSFEELRTFGGHDAKFIDSLQENEFRLYYYNKFKDIASTLNKAKSIVGTTASL
QYMKNVFKEKYLLSEDTSGKFSVDKLKFDKLYKMLTEIYTEDNFVKFFKVLNRKTYLNFDKA
VFKINIVPKVNYTIYDGFNLRNTNLAANFNGQNTEINNMNFTKLKNFTGLFEFYKLLCVRGI
I*TSKA* *(G)* $_{300}$*AGKSLVPRGSAGAG*ALNDLCIKVNNWDLFFSPSEDNFTNDLNKGEEITSDTN
IEAAEENISLDLIQQYYLTFNFDNEPENISIENLSSDIIGQLELMPNIERFPNGKKYELDKY
TMFHYLRAQEFEHGKSRIALTNSVNEALLNPSRVYTFFSSDYVKKVNKATEAAMFLGWVEQL
VYDFTDETSEVSTTDKIADITIIIPYIGPALNIGNMLYKDDFVGALIFSGAVILLEFIPEIA
IPVLGTFALVSYIANKVLTVQTIDNALSKRNEKWDEVYKYIVTNWLAKVNTQIDLIRKKMKE
ALENQAEATKAIINYQYNQYTEEEKNNINFNIDDLSSKLNESINKAMININKFLNQCSVSYL
MNSMIPYGVKRLEDFDASLKDALLKYIYDNRGTLIGQVDRLKDKVNNTLSTDIPFQLSKYVD
NQRLLSTFTEYIKNIINTSILNLRYESNHLIDLSRYASKINIGSKVNFDPIDKNQIQLFNLE
SSKIEVILKNAIVYNSMYENFSTSFWIRIPKYFNSISLNNEYTIINCMENNSGWKVSLNYGE
IIWTLQDTQEIKQRVVFKYSQMINISDYINRWIFVTITNNRLNNSKIYINGRLIDQKPISNL
GNIHASNNIMFKLDGCRDTHRYIWIKYFNLFDKELNEKEIKDLYDNQSNSGILKDFWGDYLQ
YDKPYYMLNLYDPNKYVDVNNVGIRGYMYLKGPRGSVMTTNIYLNSSLYRGTKFIIKKYASG
NKDNIVRNNDRVYINVVVKNKEYRLATNASQAGVEKILSALEIPDVGNLSQVVVMKSKNDQG
ITNKCKMNLQDNNGNDIGFIGFHQFNNIAKLVASNWYNRQIERSSRTLGCSWEFIPVDDGWG
ERPL (SEQ ID NO: 17)

MODIFIED NEUROTOXINS WITH POLY-GLYCINE AND USES THEREOF

The present invention is concerned with modified neurotoxins. Specifically, it relates to a modified biologically active neurotoxin polypeptide comprising at least one poly-Glycine domain. Also contemplated is a polynucleotide encoding the modified neurotoxin polypeptide having a poly-Glycine domain fused to the N-terminus, to the C-terminus or to both of the heavy and/or light chain of the mature neurotoxin polypeptide, vector comprising it and a host cell comprising such a polynucleotide or a vector. Moreover, envisaged are the aforementioned compounds for use as a medicament for treating various diseases.

*Clostridium botulinum* and *Clostridium tetani* produce highly potent neurotoxins, i.e. botulinum toxins (BoNTs) and tetanus toxin (TeNT), respectively. These Clostridial neurotoxins specifically bind to neuronal cells and disrupt neurotransmitter release. Each toxin is synthesized as an inactive unprocessed approximately 150 kDa single-chain protein. The posttranslational processing involves formation of disulfide bridges, and limited proteolysis (nicking) by bacterial protease(s). Active dichain neurotoxin consists of two chains, an N-terminal light chain of approx. 50 kDa and a heavy chain of approx. 100 kDa linked by a disulfide bond. Neurotoxins structurally consist of three domains, i.e. the catalytic light chain, the heavy chain encompassing the translocation domain (N-terminal half) and the receptor binding domain (C-terminal half), see Krieglstein 1990, Eur J Biochem 188, 39; Krieglstein 1991, Eur J Biochem 202, 41; Krieglstein 1994, J Protein Chem 13, 49.

*Clostridium botulinum* secretes seven antigenically distinct serotypes designated A to G of the BoNTs. All serotypes together with the related TeNT secreted by *Clostridium tetani*, are zinc ($Zn^{2+}$)-dependent endoproteases that block synaptic exocytosis by cleaving SNARE proteins and, in particular, SNAP-25. BoNTs cause, inter alia, the flaccid muscular paralysis seen in botulism and tetanus, see Fischer 2007, PNAS 104, 10447.

Despite its toxic effects, BoNTs have been used as a therapeutic agents in a large number of diseases. BoNT serotype A (BoNT/A) was approved for human use in the United States in 1989 for the treatment of strabism, blepharospasm, and other disorders. It is commercially available as a protein preparation, for example, under the tradename BOTOX (Allergan Inc) under the tradename DYSPORT (Ipsen Ltd). For therapeutic application the complex is injected directly into the muscle to be treated. At physiological pH, the toxin is released from the protein complex and the desired pharmacological effect takes place. An improved BoNT/A preparation being free of complexing proteins is available under the tradename XEOMIN (Merz Pharmaceuticals GmbH).

BoNTs, in principle, weaken voluntary muscle strength and are, therefore, effective therapeutic agents for the therapy of diseases such as strabism, focal dystonia, including cervical dystonia, and benign essential blepharospasm. They have been further shown to relief hemifacial spasm, and focal spasticity, and moreover, to be effective in a wide range of other indications, such as gastrointestinal disorders, hyperhidrosis, and cosmetic wrinkle correction, see Jost 2007, Drugs 67, 669.

However, the effect of BoNTs is only temporary, which is the reason why repeated administration of BoNTs may be required to maintain a therapeutic effect. Moreover, the more frequently these drugs are applied the higher will be the risk for an adverse immune response against the neurotoxin polypeptides applied. Further, some patients develop anti-neurotoxin antibodies and, thereby, become non-responders to therapies by conventional BoNTs. BoNTs are in some indications applied only locally. However, their diffusion potential makes a controlled local application difficult. In general, the production of these highly toxic polypeptides is cumbersome and needs special care with respect to safety issues and thus expensive. In light of these drawbacks of conventional neurotoxin polypeptides as drugs, means for improving and controlling the duration and location of the biological effective of neurotoxins would be highly appreciated for the neurotoxin therapy.

Thus, the technical problem underlying the present invention could be seen as the provision of means and methods which comply with the aforementioned needs. This technical problem has been solved by the embodiments characterized in the claims and herein below.

Accordingly, the present invention relates to a modified biologically active neurotoxin polypeptide comprising at least one poly-Glycine domain.

The term "neurotoxin polypeptide" as used herein refers to a polypeptide belonging to the antigenically different serotypes of Botulinum Neurotoxins, i.e. BoNT/A, BoNT/B, BoNT/C1, BoNT/D, BoNT/E, BoNT/F, BoNT/G, or to Tetanus Neurotoxin (TeNT). Neurotoxin polypeptides comprise an N-terminal light chain, an intermediate linker, and a C-terminal heavy chain. The neurotoxins are translated as single chain precursor molecules and become proteolytically cleaved into a mature, biologically active dichain form during processing. Proteolytic cleavage occurs at the linker in a manner such that the linker is either cleaved once or is removed after cleavage at the N- and C-termini of the linker, i.e. the N-terminal light chain or the C-terminal heavy chain.

In an aspect, the neurotoxin polypeptide (prior to the modification) comprises the light and heavy chain of a neurotoxin selected from the group consisting of: BoNT/A, BoNT/B, BoNT/C1, BoNT/D, BoNT/E, BoNT/F, BoNT/G or TeNT. In another aspect, said light and heavy chain of the neurotoxin polypeptide (prior to the modification) are encoded by a polynucleotide which comprises a nucleic acid sequence as shown in SEQ ID NO: 1 (BoNT/A), SEQ ID NO: 3 (BoNT/B), SEQ ID NO: 5 (BoNT/C1), SEQ ID NO: 7 (BoNT/D), SEQ ID NO: 9 (BoNT/E), SEQ ID NO: 11 (BoNT/F), SEQ ID NO: 13 (BoNT/G) or SEQ ID NO: 15 (TeNT). Moreover, said light and heavy chain of the neurotoxin polypeptide (prior to the modification) comprising an amino acid sequence as shown in any one of SEQ ID NO: 2 (BoNT/A), SEQ ID NO: 4 (BoNT/B), SEQ ID NO: 6 (BoNT/C1), SEQ ID NO: 8 (BoNT/D), SEQ ID NO: 10 (BoNT/E), SEQ ID NO: 12 (BoNT/F), SEQ ID NO: 14 (BoNT/G) or SEQ ID NO: 16 (TeNT).

In another aspect, the said light and heavy chain of the neurotoxin polypeptide (prior to the modification) is a variant having one or more amino acid substitutions, deletions and/or additions. Moreover, such a variant polypeptide, in an aspect, is encoded by a polynucleotide comprising a nucleic acid sequence being at least 40%, at least 50%, at least 60%, at least 70%, at least 75%, at least 80%, at least 85%, at least 90%, at least 95%, at least 98% or at least 99% identical to the nucleic acid sequence as shown in any one of SEQ ID NOs: 1, 3, 5, 7, 9, 11, 13 or 15 or a nucleic acid sequence which encodes an amino acid sequence being at least 40%, at least 50%, at least 60%, at least 70%, at least 75%, at least 80%, at least 85%, at least 90%, at least 95%, at least 98% or at least 99% identical to the amino acid sequence as shown in any one of SEQ ID NOs: 2, 4, 6, 8, 10, 12, 14, or 16. The term "identical" as used herein refers to sequence identity characterized by determining the number of identical amino acids between two nucleic acid sequences or amino acid sequences wherein the sequences are aligned so that the highest order match is obtained. It can be calculated using published techniques or methods codified in computer programs such as, for example, BLASTP, BLASTN or FASTA (Altschul 1990, J Mol Biol 215, 403). The percent identity values are, in one aspect, calculated over the entire amino acid sequence. A series of programs based on a variety of algorithms is available to the skilled worker for comparing different sequences. In this context, the algorithms of Needleman and Wunsch or Smith and Waterman give particularly reliable results. To carry out the sequence alignments, the program PileUp (Higgins 1989, CABIOS 5, 151) or the programs Gap and BestFit (Needleman 1970, J Mol Biol 48; 443; Smith 1981, Adv Appl Math 2, 482), which are part of the GCG software packet (Genetics Computer Group 1991, 575 Science Drive, Madison, Wis., USA 53711), may be used. The sequence identity values recited above in percent (%) are to be determined, in another aspect of the invention, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments. In an aspect, each of the aforementioned variant polypeptides (prior to the modification) retains one or more and, in another aspect, all of the biological properties of the respective original neurotoxin polypeptide, i.e. the BoNT/A, BoNT/B, BoNT/C1, BoNT/D, BoNT/E, BoNT/F, BoNT/G or Tetanus Neurotoxin (TeNT). Those of skill in the art will appreciate that full biological activity is maintained only after proteolytic activation, even though it is conceivable that the unprocessed precursor can exert some biological functions or be partially active. "Biological properties" as used herein refers to (a) receptor binding, (b) internalization, (c) translocation across the endosomal membrane into the cytosol, and/or (d) endoproteolytic cleavage of proteins involved in synaptic vesicle membrane fusion. In vivo assays for assessing biological activity include the mouse LD50 assay and the ex vivo mouse hemidiaphragm assay as described by Pearce et al. (Pearce 1994, Toxicol Appl Pharmacol 128: 69-77) and Dressler et al. (Dressler 2005, Mov Disord 20:1617-1619, Keller 2006, Neuroscience 139: 629-637). The biological activity is commonly expressed in Mouse Units (MU). As used herein, 1 MU is the amount of neurotoxic component, which kills 50% of a specified mouse population after intraperitoneal injection, i.e. the mouse i.p. LD50. In a further aspect, the variant polynucleotides can encode Neurotoxins having improved or altered biological properties, e.g., they may comprise cleavage sites which are improved for enzyme recognition or may be improved for receptor binding or any other property specified above.

The term "biologically active" refers to a mature neurotoxin polypeptide exhibiting essentially the biological properties specified above, i.e. being capable of a) receptor binding, (b) internalization, (c) translocation across the endosomal membrane into the cytosol, and/or (d) endoproteolytic cleavage of proteins involved in synaptic vesicle membrane fusion.

The biologically active neurotoxin polypeptide according to the present invention shall be modified in that it comprises at least one poly-Glycine domain. In an aspect, besides the poly-Glycine domain other modifications of the neurotoxin polypeptide may be envisaged in addition, including those referred to elsewhere herein.

The term "poly-Glycine domain" refers to an amino acid stretch of glycines. The said stretch comprises at least ten contiguous Glycine residues. However, it can comprise more than ten glycine residues, in an aspect, at least 20, at least 30, at least 40, at least 50, at least 100, at least 200, at least 300, at least 400 or at least 500. In an aspect, the poly-Glycine domain comprises, thus, up to 500 glycine residues. The glycine residues may also be chemically modified, e.g. by polyethylene glycol (PEG). Moreover, in an aspect said at least one poly-Glycine domain is fused to the N-terminus, to the C-terminus or to both of the heavy and/or light chain of the mature neurotoxin polypeptide. The possible positions within the single chain precursor neurotoxin polypeptide for a poly-Glycine are also exemplified in FIG. 1 A, below.

Alternatively, the said at least one poly-Glycine domain is linked to a side chain of an amino acid of the neurotoxin polypeptide. Suitable side chains encompass, in an aspect, lysine or cysteine residues, or recombinant introduced cysteine, or recombinant introduced artificial amino acids, such as ethinyl-trypthophan. The incorporation of such amino acids allows for position-specific modifications. Specifically, the said at least one poly-Glycine domain is linked, in an aspect, via an activated NHS-ester group, an activated maleimido-group, or an activated isothiocyanate-group to the side chain of an amino acid of the neurotoxin polypeptide (see, e.g., FIG. 1 B, below).

In an aspect, the modified neurotoxin polypeptide comprising the said at least one poly-Glycine domain exhibits compared to an unmodified neurotoxin polypeptide at least one of the following properties: (i) altered, i.e. increased or decreased, half-life time in a cellular system, (ii) reduced immugenicity in an organism, and/or (iii) reduced diffusion potential. It will be understood that the modified neurotoxin polypeptides according to the present invention will, in an aspect, have reduced side effects when applied to an organism.

The neurotoxin polypeptide of the invention, in an aspect, can be manufactured entirely or in part by chemical synthesis or recombinant molecular biology techniques well known for the skilled artisan. In an aspect, such a method of manufacturing the neurotoxin polypeptide of the invention comprises (a) culturing the host cell of the present invention described elsewhere herein in more detail and (b) obtaining from the said host cell the polypeptide of the present invention. In an aspect of this method, the polypeptide can be obtained by conventional purification techniques from a host cell lysate including affinity chromatography, ion exchange chromatography, size exclusion chromatography and/or preparative gel electrophoresis. The method, in an aspect may comprise proteolytical activation of the neurotoxin polypeptide. The biological activity of the activated polypeptide can be determined by the assays referred to elsewhere herein. It will be understood that in an aspect the method may comprise a step of chemically linking a poly-Glycine domain to the side chain amino acids of either the dichain proteolytically activated neurotoxin polypeptide or its single chain precursor. Moreover, it will be understood that in another aspect, where a poly-Glycine domain is fused to the N-terminus, to the C-terminus or to both of the heavy and/or light chain of the mature neurotoxin polypeptide, the said neurotoxin polypeptide can be entirely manufactured by a recombinant approach as set forth above. On the other hand, chemical linkage is necessary where the poly-Glycine domain shall be fused to an amino acid side chain.

Advantageously, the modified neurotoxin polypeptides exhibit at least one of the aforementioned properties, i.e. altered half life time in a cellular system, reduced immugenicity and or a reduced diffusion potential. Due to said properties, side effects of conventional neurotoxin polypeptides can be avoided. In particular, the neurotoxin polypeptides of the present invention can be applied in a locally more restricted manner since diffusion into other tissues is reduced. The neurotoxin polypeptides according to the present invention are, furthermore, less immunogenic and are not recognized by the immune system in patients which are sero-positive for neurotoxin antibodies. Thus, they can be applied in order to avoid immunological reactions or in sero-positive patients which are non-responders to conventional neurotoxins. Due to the reduced immugenicity, the neurotoxin polypeptides can be applied within shorter intervals and can be administered in larger amounts.

It is to be understood that the definitions and explanations of the terms made above apply mutatis mutandis for all aspects described in this specification in the following except as otherwise indicated.

The present also relates to a polynucleotide encoding the modified neurotoxin polypeptide of the present invention having a poly-Glycine domain fused to the N-terminus, to the C-terminus or to both of the heavy and/or light chain of the mature neurotoxin polypeptide.

The term "polynucleotide" as used herein refers to single- or double-stranded DNA molecules as well as to RNA molecules. Encompassed by the said term is genomic DNA, cDNA, hnRNA, mRNA as well as all naturally occurring or artificially modified derivatives of such molecular species. The polynucleotide may be in an aspect a linear or circular molecule. Moreover, in addition to the nucleic acid sequences encoding the aforementioned neurotoxin polypeptide, a polynucleotide of the present invention may comprise additional sequences required for proper transcription and/or translation such as 5'- or 3'-UTR sequences.

Moreover, the present invention relates to a vector comprising the polynucleotide of the present invention. In an aspect, the said vector is an expression vector.

The term "vector", preferably, encompasses phage, plasmid, viral or retroviral vectors as well as artificial chromosomes, such as bacterial or yeast artificial chromosomes. Moreover, the term also relates to targeting constructs which allow for random or site-directed integration of the targeting construct into genomic DNA. Such target constructs, preferably, comprise DNA of sufficient length for either homologous or heterologous recombination as described in detail below. The vector encompassing the polynucleotides of the present invention, in an aspect, further comprises selectable markers for propagation and/or selection in a host. The vector may be incorporated into a host cell by various techniques well known in the art. For example, a plasmid vector can be introduced in a precipitate such as a calcium phosphate precipitate or rubidium chloride precipitate, or in a complex with a charged lipid or in carbon-based clusters, such as fullerens. Alternatively, a plasmid vector may be introduced by heat shock or electroporation techniques. Should the vector be a virus, it may be packaged in vitro using an appropriate packaging cell line prior to application to host cells. Retroviral vectors may be replication competent or replication defective. In the latter case, viral propagation generally will occur only in complementing host/cells. Moreover, in an aspect of the invention, the polynucleotide is operatively linked to expression control sequences allowing expression in prokaryotic or eukaryotic host cells or isolated fractions thereof in the said vector. Expression of the polynucleotide comprises transcription of the polynucleotide into a translatable mRNA. Regulatory elements ensuring expression in host cells are well known in the art. In an aspect, they comprise regulatory sequences ensuring initiation of transcription and/or poly-A signals ensuring termination of transcription and stabilization of the transcript. Additional regulatory elements may include transcriptional as well as translational enhancers. Possible regulatory elements permitting expression in prokaryotic host cells comprise, e.g., the lac-, trp- or tac-promoter in *E. coli*, and examples for regulatory elements permitting expression in eukaryotic host cells are the AOX1- or the GAL1-promoter in yeast or the CMV-, SV40-, RSV-promoter (Rous sarcoma virus), CMV-enhancer, SV40-enhancer or a globin intron in mammalian and other animal cells. Other expression systems envisaged by the invention shall permit expression in insect cells, such as polyhedrin promoter based systems.

Moreover, inducible expression control sequences may be used in an expression vector encompassed by the present invention. Such inducible vectors may comprise tet or lac operator sequences or sequences inducible by heat shock or other environmental factors. Suitable expression control sequences are well known in the art. Beside elements which are responsible for the initiation of transcription such regulatory elements may also comprise transcription termination signals, such as the SV40-poly-A site or the tk-poly-A site, downstream of the polynucleotide. In this context, suitable expression vectors are known in the art such as Okayama-Berg cDNA expression vector pcDV1 (Pharmacia), pBluescript (Stratagene), pCDM8, pRc/CMV, pcDNA1, pcDNA3 (Invitrogen) or pSPORT1 (Invitrogen) or baculovirus-derived vectors. Preferably, said vector is an expression vector and a gene transfer or targeting vector. Expression vectors derived from viruses such as retroviruses, vaccinia virus, adeno-associated virus, herpes viruses, or bovine papilloma virus, may be used for delivery of the polynucleotides or vector of the invention into targeted cell population. Methods which are well known to those skilled in the art can be used to construct recombinant viral vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994).

The present invention contemplates a host cell comprising the polypeptide, the polynucleotide, or the vector of the present invention.

The term "host cell" as used herein encompasses prokaryotic and eukaryotic host cells. In an aspect the host cell is a bacterial cell and, in another aspect, a Firmicutes bacterial cell. In one aspect, the said bacterial host cell is an *E. coli* host cell. In another aspect, it is a *Clostridium* host cell. In a further aspect, the said *Clostridium* host cell is a *Clostridium botulinum* host cell, in even a further aspect, a cell of one of the aforementioned seven different serotypes of *Clostridium botulinum*. In yet another aspect, the bacterial host cell is a *Clostridium tetani* host cell. In a further aspect, the host cell is a *Bacillus* host cell and in a particular aspect a *Bacillus megaterium* host cell. A eukaryotic host cell, in an aspect, is a cell of an animal cell line suitable for production of toxic proteins or a fungal host cell such as a yeast host cell. A host cell as referred to herein, thus, encompasses in an aspect yeast, mammalian, plant or insect cells either as primary cells or as cell lines.

The present invention encompasses a composition comprising the polypeptide, the polynucleotide, or the vector of the present invention as a medicament.

The term "medicament" as used herein refers, in one aspect, to a pharmaceutical composition containing the polypeptide, polynucleotide or vector of the present invention as pharmaceutical active compound, wherein the pharmaceutical composition may be used for human or non-human therapy of various diseases or disorders in a therapeutically effective dose.

In an aspect, the polypeptide, polynucleotide or vector of the present invention can be present in liquid or lyophilized form. In an aspect, said compound can be present together with glycerol, protein stabilizers (e.g., human serum albumin (HSA)) or non-protein stabilizers.

The medicament is, in one aspect, administered topically. Conventionally used drug administration is administered intra-muscular, subcutaneous (near glands). However, depending on the nature and the mode of action of a compound (i.e. the polypeptide, polynucleotide or vector of the present invention), the medicament may be administered by other routes as well.

The compound is the active ingredient of the composition, and is in one aspect, administered in conventional dosage forms prepared by combining the drug with standard pharmaceutical carriers according to conventional procedures. These procedures may involve mixing, granulating, and compression, or dissolving the ingredients as appropriate to the desired preparation. It will be appreciated that the form and character of the pharmaceutical acceptable carrier or diluent is dictated by the amount of active ingredient with which it is to be combined, the route of administration, and other well-known variables.

The carrier(s) must be acceptable in the sense of being compatible with the other ingredients of the formulation and being not deleterious to the recipient thereof. The pharmaceutical carrier employed may include a solid, a gel, or a liquid. Exemplary of solid carriers are lactose, terra alba, sucrose, talc, gelatin, agar, pectin, acacia, magnesium stearate, stearic acid and the like. Exemplary of liquid carriers are phosphate buffered saline solution, syrup, oil, water, emulsions, various types of wetting agents, and the like. Similarly, the carrier or diluent may include time delay material well known to the art, such as glyceryl mono-stearate or glyceryl distearate alone or with a wax. Said suitable carriers comprise those mentioned above and others well known in the art, see, e.g., Remington's Pharmaceutical Sciences, Mack Publishing Company, Easton, Pa.

The diluent(s) is/are selected so as not to affect the biological activity of the combination. Examples of such diluents are distilled water, physiological saline, Ringer's solutions, dextrose solution, and Hank's solution. In addition, the pharmaceutical composition or formulation may also include other carriers, adjuvants, or non-toxic, non-therapeutic, non-immunogenic stabilizers and the like.

A therapeutically effective dose refers to an amount of the compound to be used in medicament of the present invention which prevents, ameliorates or treats the symptoms accompanying a disease or condition referred to in this specification. Therapeutic efficacy and toxicity of the compound can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50.

The dosage regimen will be determined by the attending physician and other clinical factors. As is well known in the medical arts, dosages for any one patient depends upon many factors, including the patient's size, body surface area, age, the particular compound to be administered, sex, time and route of administration, general health, and other drugs being administered concurrently. Progress can be monitored by periodic assessment.

The medicament referred to herein is administered at least once in order to treat or ameliorate or prevent a disease or condition recited in this specification. However, the said medicament may be administered more than one time.

Specific medicaments are prepared in a manner well known in the pharmaceutical art and comprise at least one active compound referred to herein above in admixture or otherwise associated with a pharmaceutically acceptable carrier or diluent. For making those specific pharmaceutical compositions, the active compound(s) will usually be mixed with a carrier or the diluent. The resulting formulations are to be adapted to the mode of administration. Dosage recommendations shall be indicated in the prescribers or users instructions in order to anticipate dose adjustments depending on the considered recipient.

The medicament according to the present invention may in a further aspect of the invention comprise drugs in addition to the polypeptide, polynucleotide or vector of the present invention which are added to the medicament during its formulation. Finally, it is to be understood that the formulation of a medicament takes place under GMP standardized conditions or the like in order to ensure quality, pharmaceutical security, and effectiveness of the medicament.

Contemplated by the present invention is also a composition comprising the polypeptide, the polynucleotide, or the vector of the present invention to be used for treating and/or preventing a disease selected from the group consisting of: voluntary muscle strength, focal dystonia, including cervical, cranial dystonia, and benign essential blepharospasm, hemifacial spasm, and focal spasticity, gastrointestinal disorders, hyperhidrosis, and cosmetic wrinkle correction, Blepharospasm, oromandibular dystonia, jaw opening type, jaw closing type, bruxism, Meige syndrome, lingual dystonia, apraxia of eyelid, opening cervical dystonia, antecollis, retrocollis, laterocollis, torticollis, pharyngeal dystonia, laryngeal dystonia, spasmodic dysphonia/adductor type, spasmodic dysphonia/abductor type, spasmodic dyspnea, limb dystonia, arm dystonia, task specific dystonia, writer's cramp, musician's cramps, golfer's cramp, leg dystonia, thigh adduction, thigh abduction knee flexion, knee extension, ankle flexion, ankle extension, equinovarus, deformity foot dystonia, striatal toe, toe flexion, toe extension, axial dystonia, pisa syndrome, belly dancer dystonia, segmental dystonia, hemidystonia, generalised dystonia, dystonia in lubag, dystonia in corticobasal degeneration, dystonia in lubag, tardive dystonia, dystonia in spinocerebellar ataxia, dystonia in Parkinson's disease, dystonia in Huntington's disease, dystonia in Hallervorden-Spatz disease, dopa-induced dyskinesias/dopa-induced dystonia, tardive dyskinesias/tardive dystonia, paroxysmal dyskinesias/dystonias, kinesiogenic non-kinesiogenic action-induced palatal myoclonus, myoclonus myokymia, rigidity, benign muscle cramps, hereditary chin trembling, paradoxic jaw muscle activity, hemimasticatory spasms, hypertrophic branchial myopathy, maseteric hypertrophy, tibialis anterior hypertrophy, nystagmus, oscillopsia supranuclear gaze palsy, epilepsia, partialis continua, planning of spasmodic torticollis operation, abductor vocal cord paralysis, recalcitant mutational dysphonia, upper oesophageal sphincter dysfunction, vocal fold granuloma, stuttering Gilles de la Tourette syndrome, middle ear myoclonus, protective larynx closure, postlaryngectomy, speech failure, protective ptosis, entropion sphincter Odii dysfunction, pseudoachalasia, nonachalsia, oesophageal motor disorders, vaginismus, postoperative immobilisation tremor, bladder dysfunction, detrusor sphincter dyssynergia, bladder sphincter spasm, hemifacial spasm, reinnervation dyskinesias, cosmetic use craw's feet, frowning facial asymmetries, mentalis dimples, stiff person syndrome, tetanus prostate hyperplasia, adipositas, treatment infantile cerebral palsy strabismus, mixed paralytic concomitant, after retinal detachment surgery, after cataract surgery, in aphakia myositic strabismus, myopathic strabismus, dissociated vertical deviation, as an adjunct to strabismus surgery, esotropia, exotropia, achalasia, anal fissures, exocrine gland hyperactivity, Frey syndrome, Crocodile Tears syndrome, hyperhidrosis, axillar palmar plantar rhinorrhea, relative hypersalivation in stroke, in Parkinsosn's, in amyotrophic lateral sclerosis, spastic conditions, in encephalitis and myelitis autoimmune processes, multiple sclerosis, transverse myelitis, Devic syndrome, viral infections, bacterial infections, parasitic infections, fungal infections, in hereditary spastic paraparesis postapoplectic syndrome hemispheric infarction, brainstem infarction, myelon infarction, in central nervous system trauma, hemispheric lesions, brainstem lesions, myelon lesion, in central nervous system hemorrhage, intracerebral hemorrhage, subarachnoidal hemorrhage, subdural hemorrhage, intraspinal hemorrhage, in neoplasias, hemispheric tumors, brainstem tumors, and myelon tumor.

The present invention relates to a method for the manufacture of a medicament comprising formulating a composition comprising the polypeptide, the polynucleotide or the vector of the preset invention in a pharmaceutically acceptable form.

In an aspect, the said medicament is to be applied for treating a disease selected from the group consisting of: voluntary muscle strength, focal dystonia, including cervical, cranial dystonia, and benign essential blepharospasm, hemifacial spasm, and focal spasticity, gastrointestinal disorders, hyperhidrosis, and cosmetic wrinkle correction, Blepharospasm, oromandibular dystonia, jaw opening type, jaw closing type, bruxism, Meige syndrome, lingual dystonia, apraxia of eyelid, opening cervical dystonia, antecollis, retrocollis, laterocollis, torticollis, pharyngeal dystonia, laryngeal dystonia, spasmodic dysphonia/adductor type, spasmodic dysphonia/abductor type, spasmodic dyspnea, limb dystonia, arm dystonia, task specific dystonia, writer's cramp, musician's cramps, golfer's cramp, leg dystonia, thigh adduction, thigh abduction knee flexion, knee extension, ankle flexion, ankle extension, equinovarus, deformity foot dystonia, striatal toe, toe flexion, toe extension, axial dystonia, pisa syndrome, belly dancer dystonia, segmental dystonia, hemidystonia, generalised dystonia, dystonia in lubag, dystonia in corticobasal degeneration, dystonia in lubag, tardive dystonia, dystonia in spinocerebellar ataxia, dystonia in Parkinson's disease, dystonia in Huntington's disease, dystonia in Hallervorden-Spatz disease, dopa-induced dyskinesias/dopa-induced dystonia, tardive dyskinesias/tardive dystonia, paroxysmal dyskinesias/dystonias, kinesiogenic non-kinesiogenic action-induced palatal myoclonus, myoclonus myokymia, rigidity, benign muscle cramps, hereditary chin trembling, paradoxic jaw muscle activity, hemimasticatory spasms, hypertrophic branchial myopathy, maseteric hypertrophy, tibialis anterior hypertrophy, nystagmus, oscillopsia supranuclear gaze palsy, epilepsia, partialis continua, planning of spasmodic torticollis operation, abductor vocal cord paralysis, recalcitant mutational dysphonia, upper oesophageal sphincter dysfunction, vocal fold granuloma, stuttering Gilles de la Tourette syndrome, middle ear myoclonus, protective larynx closure, postlaryngectomy, speech failure, protective ptosis, entropion sphincter Odii dysfunction, pseudoachalasia, nonachalsia, oesophageal motor disorders, vaginismus, postoperative immobilisation tremor, bladder dysfunction, detrusor sphincter dyssynergia, bladder sphincter spasm, hemifacial spasm, reinnervation dyskinesias, cosmetic use craw's feet, frowning facial asymmetries, mentalis dimples, stiff person syndrome, tetanus prostate hyperplasia, adipositas, treatment infantile cerebral palsy strabismus, mixed paralytic concomitant, after retinal detachment surgery, after cataract surgery, in aphakia myositic strabismus, myopathic strabismus, dissociated vertical deviation, as an adjunct to strabismus surgery, esotropia, exotropia, achalasia, anal fissures, exocrine gland hyperactivity, Frey syndrome, Crocodile Tears syndrome, hyperhidrosis, axillar palmar plantar rhinorrhea, relative hypersalivation in stroke, in Parkinsosn's, in amyotrophic lateral sclerosis, spastic conditions, in encephalitis and myelitis autoimmune processes, multiple sclerosis, transverse myelitis, Devic syndrome, viral infections, bacterial infections, parasitic infections, fungal infections, in hereditary spastic paraparesis postapoplectic syndrome hemispheric infarction, brainstem infarction, myelon infarction, in central nervous system trauma, hemispheric lesions, brainstem lesions, myelon lesion, in central nervous system hemorrhage, intracerebral hemorrhage, subarachnoidal hemorrhage, subdural hemorrhage, intraspinal hemorrhage, in neoplasias, hemispheric tumors, brainstem tumors, and myelon tumor.

In yet another aspect, the aforementioned composition further comprises an agent which governs a sustained release of the polypeptide, polynucleotide, or vector.

The term "sustained release" as used herein refers to a controlled release of the active ingredient with respect to time and amount. In an aspect, it is envisaged that a certain amount is released continuously over a certain time rather than a release as a single bolus. Alternatively, a release may take place by various bolus releases over a certain time. Agents which can govern sustained release are known in the art for the different ingredients and include polymers which can for hydrogels as depositories for the ingredients. Suitable polymers, in an aspect, are selected from alginates, hyaluronic acid, dextrane, agarose, polyethylene glycol, and the like. Other agents to be applied in this context are semi-permeable materials such as semi-permeable membranes governing the release of the active ingredients from a depository.

In another aspect of the invention, the composition is a cosmetic composition which can be formulated as described for a medicament above. For a cosmetic composition, likewise, it is envisaged that the compound of the present invention is in an aspect used in substantially pure form. Cosmetic compositions are, in a further aspect, to be applied intramuscular. In an even further aspect of the invention, cosmetic compositions comprising the neurotoxin can be formulated as an anti-wrinkle solution.

All references cited in this specification are herewith incorporated by reference with respect to their entire disclosure content and the disclosure content specifically mentioned in this specification.

FIGURES

FIG. 1 shows a schematic drawing of poly-Glycine domains introduced into the amino acid chain of the neurotoxin precursor molecule (A) or poly-Glycine domains which are chemically linked to the side chain (B); abbreviations: LC=light chain, HC=heavy chain, pGly=poly-Glycine domain.

FIG. 2 shows the poly-Glycine modified neurotoxin polypeptide, whereby the BoNT/A light chain is indicated by a dashed underlining and the BoNT/A heavy chain is black underlined. The linker region is indicated by italic amino acid sequences and comprises the poly-Glycine domain $((G)_{300})$ and the thrombin proteolytic site which is indicated by bold letters (LVPRGS, SEQ ID NO: 18). Said thrombin proteolytic site is required for the activation of the polypeptide after is has been produced in *E. coli.*

EXAMPLES

The invention will now be described by the following, non-limiting Examples which merely illustrate the invention but shall not be construed as limiting its scope.

Example 1

Cloning of a Poly-Glycine Modified Neurotoxin Polypeptide

The poly-Glycine modified neurotoxin polypeptide is produced by chemical synthesis, e.g., analogous to poly-l-lysine. Alternatively, the poly-Glycine modified neurotoxin polypeptide is manufactured recombinantly. The latter can be achieved by use of a codon-optimized DNA construct which is produced using gene synthesis, such as a DNA construct encoding the polypeptide which is represented in FIG. 2 and shown in SEQ ID NO: 17. Said polypeptide comprises inter alia a BoNT/A light chain, a BoNT/A heavy chain, and a poly-Glycine domain within the linker.

Further, the poly-Glycine modified neurotoxin polypeptide is produced by introducing an additional cysteine instead the above mentioned recombinant poly-Glycine domain within the linker region (see SEQ ID NO: 17). Thus, after thrombin cleavage at the defined region LVPRGS (SEQ ID NO: 18) recombinant produced or chemical synthesized poly-Glycin can be bound to the additional cysteine residue using maleimide-thiol coupling.

The above mentioned DNA construct is cloned using, preferably, standard expression vectors, such as pET-system cloning by Novagen, pASK-vectors by IBA, and the like.

The invention claimed is:

1. A modified biologically active neurotoxin polypeptide comprising at least one poly-Glycine domain in the linker region.

2. The polypeptide of claim 1, wherein the modified neurotoxin polypeptide comprising the at least one poly-Glycine domain exhibits, compared to an unmodified neurotoxin polypeptide, at least one of the following properties: (i) altered half-life time in a cellular system, (ii) reduced immunogenicity in an organism, and/or (iii) reduced diffusion potential.

3. The polypeptide of claim 1, wherein the at least one poly-Glycine domain is linked to a side chain of an amino acid of the neurotoxin polypeptide.

4. The polypeptide of claim 3, wherein the at least one poly-Glycine domain is linked via an activated NHS-ester group, an activated maleimido-group, or an activated isothiocyanate-group.

5. A polynucleotide encoding the modified neurotoxin polypeptide of claim 1 comprising a poly-Glycine domain fused to the N-terminus, to the C-terminus or to both of a heavy and/or light chain of the mature neurotoxin polypeptide.

6. A vector comprising the polynucleotide of claim 5.

7. The vector of claim 6, wherein the vector is an expression vector.

8. An in vitro protein expression system host cell comprising the polypeptide of claim 1.

9. A method for treating a disease, comprising administering to a subject in the need thereof a therapeutically effective amount of a composition comprising the polypeptide of claim 1, thereby treating and/or preventing the disease in the subject, wherein the disease is selected from the group consisting of: voluntary muscle strength, focal dystonia, cervical dystonia, cranial dystonia, benign essential blepharospasm, hemifacial spasm, focal spasticity, gastrointestinal disorders, hyperhidrosis, cosmetic wrinkle correction, blepharospasm, oromandibular dystonia of the jaw opening type, oromandibular dystonia of the jaw closing type, bruxism, Meige syndrome, lingual dystonia, apraxia of eyelid, opening cervical dystonia, antecollis, retrocollis, laterocoilis, torticollis, pharyngeal dystonia, laryngeal dystonia, spasmodic dysphonia/adductor type, spasmodic dysphonia/abductor type, spasmodic dyspnea, limb dystonia, arm dystonia, task specific dystonia, writer's cramp, musician's cramps, golfer's cramp, leg dystonia, thigh adduction, thigh abduction knee flexion, knee extension, ankle flexion, ankle extension, equinovarus, deformity foot dystonia, striatal toe, toe flexion, toe extension, axial dystonia, pisa syndrome, belly dancer dystonia, segmental dystonia, hemidystonia, generalized dystonia, dystonia in lubag, dystonia in corticobasal degeneration, dystonia in lubag, tardive dystonia, dystonia in spinocerebellar ataxia, dystonia in Parkinson's disease, dystonia in Huntington's disease, dystonia in Hallervorden-Spatz disease, dopa-induced dyskinesias/dopa-induced dystonia, tardive dyskinesias/tardive dystonia, paroxysmal dyskinesias/dystonias, kinesiogenic non-kinesiogenic action-induced palatal myoclonus, myoclonus myokymia, rigidity, benign muscle cramps, hereditary chin trembling, paradoxic jaw muscle activity, hemimasticatory spasms, hypertrophic branchial myopathy, maseteric hypertrophy, tibialis anterior hypertrophy, nystagmus, oscillopsia supranuclear gaze palsy, epilepsia, partialis continua, planning of spasmodic torticollis operation, abductor vocal cord paralysis, recalcitrant mutational dysphonia, upper oesophageal sphincter dysfunction, vocal fold granuloma, stuttering Gilles de la Tourette syndrome, middle ear myoclonus, protective larynx closure, postlaryngectomy, speech failure, protective ptosis, entropion sphincter Odii dysfunction, pseudoachalasia, nonachaisia, oesophageal motor disorders, vaginismus, postoperative immobilization, tremor, bladder dysfunction, detrusor sphincter dyssynergia, bladder sphincter spasm, hemifacial spasm, reinnervation dyskinesias, crow's feet, frowning facial asymmetries, mentalis dimples, stiff person syndrome, tetanus prostate hyperplasia, adipositas, treatment infantile cerebral palsy strabismus, mixed paralytic concomitant, after retinal detachment surgery, after cataract surgery, in aphakia myositic strabismus, myopathic strabismus, dissociated vertical deviation, as an adjunct to strabismus surgery, esotropia, exotropia, achalasia, anal fissures, exocrine gland hyperactivity, Frey syndrome, crocodile tears syndrome, axillar palmar plantar rhinorrhea, relative hypersalivation in stroke, in Parkinson's disease, and in amyotrophic lateral sclerosis, spastic conditions, in encephalitis and myelitis autoimmune processes, multiple sclerosis, transverse myelitis, Devic syndrome, viral infections, bacterial infections, parasitic infections, fungal infections, in hereditary spastic paraparesis postapoplectic syndrome hemispheric infarction, brainstem infarction, myelon infarction, in central nervous system trauma, hemispheric lesions, brainstem lesions, myelon lesion, in central nervous system hemorrhage, intracerebral hemorrhage, subarachnoidal hemorrhage, subdural hemorrhage, intraspinal hemorrhage, in neoplasias, hemispheric tumors, brainstem tumors, and myelon tumor.

10. A method for the manufacture of a medicament comprising formulating a composition comprising the polypeptide of claim 1, in a pharmaceutically acceptable form.

11. The method of claim 10, wherein the medicament is administered to a subject in the need thereof in a therapeutically effective amount for treating a disease selected from the group consisting of: voluntary muscle strength, focal dystonia, including cervical, cranial dystonia, and benign essential blepharospasm, hemifacial spasm, and focal spasticity, gastrointestinal disorders, hyperhidrosis, and cosmetic wrinkle correction, blepharospasm, oromandibular dystonia of the jaw opening type, oromandibular dystonia of the jaw dosing type, bruxism, Meige syndrome, lingual dystonia, apraxia of eyelid, opening cervical dystonia, antecollis, retrocollis, laterocollis, torticollis, pharyngeal dystonia, laryngeal dystonia, spasmodic dysphonia/adductor type, spasmodic dysphonia/abductor type, spasmodic dyspnea, limb dystonia, arm dystonia, task specific dystonia, writer's cramp, musician's cramps, golfer's cramp, leg dystonia, thigh adduction, thigh abduction knee flexion, knee extension, ankle flexion, ankle extension, equinovarus, deformity foot dystonia, striatal toe, toe flexion, toe extension, axial dystonia, pisa syndrome, belly dancer dystonia, segmental dystonia, hemidystonia, generalised dystonia, dystonia in lubag, dystonia in corticobasal degeneration, dystonia in lubag, tardive dystonia, dystonia in spinocerebellar ataxia, dystonia in Parkinson's disease, dystonia in Huntington's disease, dystonia in Hallervorden-Spatz disease, dopa-induced dyskinesia/dopa-induced dystonia, tardive dyskinesias/tardive dystonia, paroxysmal dyskinesias/dystonias, kinesiogenic non-kinesiogenic action-induced palatal myoclonus, myoclonus myokymia, rigidity, benign muscle cramps, hereditary chin trembling, paradoxic jaw muscle activity, hemimasticatory spasms, hypertrophic branchial myopathy, maseteric hypertrophy, tibialis anterior hypertrophy, nystagmus, oscillopsia supranuclear gaze palsy, epilepsia, partialis continua, planning of spasmodic torticollis operation, abductor vocal cord paralysis, recalcitrant mutational dysphonia, upper oesophageal sphincter dysfunction, vocal fold granuloma, stuttering Gilles de la Tourette syndrome, middle ear myoclonus, protective larynx closure, postiaryngectomy, speech failure, protective ptosis, entropion sphincter Odii dysfunction, pseudoachalasia, nonachalsia, oesophageal motor disorders, vaginismus, postoperative immobilisation tremor, bladder dysfunction, detrusor sphincter dyssynergia, bladder sphincter spasm, hemifacial spasm, reinnervation dyskinesias, cosmetic use craw's feet, frowning facial asymmetries, mentalis dimples, stiff person syndrome, tetanus prostate hyperplasia, adipositas, treatment infantile cerebral palsy strabismus, mixed paralytic concomitant, after retinal detachment surgery, after cataract surgery, in aphakia myositic strabismus, myopathic strabismus, dissociated vertical deviation, as an adjunct to strabismus surgery, esotropia, exotropia, achalasia, anal fissures, exocrine gland hyperactivity, Frey syndrome, Crocodile Tears syndrome, axillar palmar plantar rhinorrhea, relative hypersalivation in stroke, relative hypersalivation in Parkinson's disease, relative hypersalivation in amyotrophic lateral sclerosis, spastic conditions, in encephalitis and myelitis autoimmune processes, multiple sclerosis, transverse myelitis, Devic syndrome, viral infections, bacterial infections, parasitic infections, fungal infections, in hereditary spastic paraparesis postapoplectic syndrome hemispheric infarction, brainstem infarction, myelon infarction, in central nervous system trauma, hemispheric lesions, brainstem lesions, myelon lesion, in central nervous system hemorrhage, intracerebral hemorrhage, subarachnoidal hemorrhage, subdural hemorrhage, intraspinal hemorrhage, in neoplasias, hemispheric tumors, brainstem tumors, and myelon tumor.

12. The method of claim 9, wherein the composition further comprises an agent which governs a sustained release of the polypeptide.

* * * * *

SEQUENCE LISTING

```
<160> NUMBER OF SEQ ID NOS: 18

<210> SEQ ID NO 1
<211> LENGTH: 3891
<212> TYPE: DNA
<213> ORGANISM: Clostridium botulinum

<400> SEQUENCE: 1

atgccatttg ttaataaaca atttaattat aaagatcctg taaatggtgt tgatattgct     60

tatataaaaa ttccaaatgc aggacaaatg caaccagtaa aagcttttaa aattcataat    120

aaaatatggg ttattccaga aagagataca tttacaaatc ctgaagaagg agatttaaat    180

ccaccaccag aagcaaaaca agttccagtt tcatattatg attcaacata tttaagtaca    240

gataatgaaa aagataatta tttaaaggga gttacaaaat tatttgagag aatttattca    300

actgatcttg gaagaatgtt gttaacatca atagtaaggg gaataccatt ttggggtgga    360

agtacaatag atacagaatt aaaagttatt gatactaatt gtattaatgt gatacaacca    420

gatggtagtt atagatcaga agaacttaat ctagtaataa taggaccctc agctgatatt    480

atacagtttg aatgtaaaag ctttggacat gaagttttga atcttacgcg aaatggttat    540

ggctctactc aatacattag atttagccca gattttacat ttggttttga ggagtcactt    600

gaagttgata caaatcctct tttaggtgca ggcaaatttg ctacagatcc agcagtaaca    660

ttagcacatg aacttataca tgctggacat agattatatg gaatagcaat taatccaaat    720

agggttttta aagtaaatac taatgcctat tatgaaatga gtgggttaga agtaagcttt    780

gaggaactta gaacatttgg gggacatgat gcaaagttta tagatagttt acaggaaaac    840

gaatttcgtc tatattatta taataagttt aaagatatag caagtacact taataaagct    900

aaatcaatag taggtactac tgcttcatta cagtatatga aaaatgtttt taaagagaaa    960

tatctcctat ctgaagatac atctggaaaa ttttcggtag ataaattaaa atttgataag   1020

ttatacaaaa tgttaacaga gatttacaca gaggataatt ttgttaagtt ttttaaagta   1080

cttaacagaa aaacatattt gaattttgat aaagccgtat ttaagataaa tatagtacct   1140

aaggtaaatt acacaatata tgatggattt aatttaagaa atacaaattt agcagcaaac   1200

tttaatggtc aaaatacaga aattaataat atgaatttta ctaaactaaa aaattttact   1260

ggattgtttg aattttataa gttgctatgt gtaagaggga taataacttc taaaactaaa   1320

tcattagata aaggatacaa taaggcatta aatgatttat gtatcaaagt taataattgg   1380
```

-continued

```
gacttgtttt ttagtccttc agaagataat tttactaatg atctaaataa aggagaagaa   1440
attacatctg atactaatat agaagcagca gaagaaaata ttagtttaga tttaatacaa   1500
caatattatt taacctttaa ttttgataat gaacctgaaa atatttcaat agaaaatctt   1560
tcaagtgaca ttataggcca attagaactt atgcctaata tagaaagatt tcctaatgga   1620
aaaaagtatg agttagataa atatactatg ttccattatc ttcgtgctca agaatttgaa   1680
catggtaaat ctaggattgc tttaacaaat tctgttaacg aagcattatt aaatcctagt   1740
cgtgtttata cattttttc ttcagactat gtaaagaaag ttaataaagc tacggaggca   1800
gctatgtttt taggctgggt agaacaatta gtatatgatt ttaccgatga aactagcgaa   1860
gtaagtacta cggataaaat tgcggatata actataatta ttccatatat aggacctgct   1920
ttaaatatag gtaatatgtt atataaagat gattttgtag gtgctttaat attttcagga   1980
gctgttattc tgttagaatt tataccagag attgcaatac ctgtattagg tacttttgca   2040
cttgtatcat atattgcgaa taaggttcta accgttcaaa caatagataa tgctttaagt   2100
aaaagaaatg aaaaatggga tgaggtctat aaatatatag taacaaattg gttagcaaag   2160
gttaatacac agattgatct aataagaaaa aaaatgaaag aagctttaga aaatcaagca   2220
gaagcaacaa aggctataat aaactatcag tataatcaat atactgagga agagaaaaat   2280
aatattaatt ttaatattga tgatttaagt tcgaaactta atgagtctat aaataaagct   2340
atgattaata taaataaatt tttgaatcaa tgctctgttt catatttaat gaattctatg   2400
atcccttatg gtgttaaacg gttagaagat tttgatgcta gtcttaaaga tgcattatta   2460
aagtatatat atgataatag aggaacttta attggtcaag tagatagatt aaaagataaa   2520
gttaataata cacttagtac agatatacct tttcagcttt ccaaatacgt agataatcaa   2580
agattattat ctacatttac tgaatatatt aagaatatta ttaatacttc tatattgaat   2640
ttaagatatg aaagtaatca tttaatagac ttatctaggt atgcatcaaa aataaatatt   2700
ggtagtaaag taaattttga tccaatagat aaaaatcaaa ttcaattatt taatttagaa   2760
agtagtaaaa ttgaggtaat tttaaaaaat gctattgtat ataatagtat gtatgaaaat   2820
tttagtacta gcttttggat aagaattcct aagtatttta acagtataag tctaaataat   2880
gaatatacaa taataaattg tatggaaaat aattcaggat ggaaagtatc acttaattat   2940
ggtgaaataa tctggacttt acaggatact caggaaataa aacaaagagt agtttttaaa   3000
tacagtcaaa tgattaatat atcagattat ataaacagat ggatttttgt aactatcact   3060
aataatagat taaataactc taaaatttat ataaatggaa gattaataga tcaaaaacca   3120
atttcaaatt taggtaatat tcatgctagt aataatataa tgtttaaatt agatggttgt   3180
agagatacac atagatatat ttggataaaa tattttaatc tttttgataa ggaattaaat   3240
gaaaaagaaa tcaaagattt atatgataat caatcaaatt caggtatttt aaaagacttt   3300
tggggtgatt atttacaata tgataaacca tactatatgt taaatttata tgatccaaat   3360
aaatatgtcg atgtaaataa tgtaggtatt agaggttata tgtatcttaa agggcctaga   3420
ggtagcgtaa tgactacaaa catttattta aattcaagtt tgtatagggg gacaaaattt   3480
attataaaaa aatatgcttc tggaaataaa gataatattg ttagaaataa tgatcgtgta   3540
tatattaatg tagtagttaa aaataaagaa tataggttag ctactaatgc atcacaggca   3600
ggcgtagaaa aaatactaag tgcattagaa atacctgatg taggaaatct aagtcaagta   3660
gtagtaatga agtcaaaaaa tgatcaagga ataacaaata aatgcaaaat gaatttacaa   3720
gataataatg ggaatgatat aggctttata ggatttcatc agtttaataa tatagctaaa   3780
```

```
ctagtagcaa gtaattggta taatagacaa atagaaagat ctagtaggac tttgggttgc   3840

tcatgggaat ttattcctgt agatgatgga tggggagaaa ggccactgta a            3891


<210> SEQ ID NO 2
<211> LENGTH: 1296
<212> TYPE: PRT
<213> ORGANISM: Clostridium botulinum

<400> SEQUENCE: 2

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350
```

```
Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
        435                 440                 445

Ala Leu Asn Asp Leu Cys Ile Lys Val Asn Asn Trp Asp Leu Phe Phe
    450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
        515                 520                 525

Glu Leu Met Pro Asn Ile Glu Arg Phe Pro Asn Gly Lys Lys Tyr Glu
    530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
        595                 600                 605

Gln Leu Val Tyr Asp Phe Thr Asp Glu Thr Ser Glu Val Ser Thr Thr
    610                 615                 620

Asp Lys Ile Ala Asp Ile Thr Ile Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
    690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
        755                 760                 765

Leu Ser Ser Lys Leu Asn Glu Ser Ile Asn Lys Ala Met Ile Asn Ile
```

```
    770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
    850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
                885                 890                 895

Lys Ile Asn Ile Gly Ser Lys Val Asn Phe Asp Pro Ile Asp Lys Asn
            900                 905                 910

Gln Ile Gln Leu Phe Asn Leu Glu Ser Ser Lys Ile Glu Val Ile Leu
        915                 920                 925

Lys Asn Ala Ile Val Tyr Asn Ser Met Tyr Glu Asn Phe Ser Thr Ser
    930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Leu Gln Asp Thr Gln Glu
            980                 985                 990

Ile Lys Gln Arg Val Val Phe Lys  Tyr Ser Gln Met Ile  Asn Ile Ser
        995                 1000                1005

Asp Tyr  Ile Asn Arg Trp Ile  Phe Val Thr Ile Thr  Asn Asn Arg
    1010                1015                1020

Leu Asn  Asn Ser Lys Ile Tyr  Ile Asn Gly Arg Leu  Ile Asp Gln
    1025                1030                1035

Lys Pro  Ile Ser Asn Leu Gly  Asn Ile His Ala Ser  Asn Asn Ile
    1040                1045                1050

Met Phe  Lys Leu Asp Gly Cys  Arg Asp Thr His Arg  Tyr Ile Trp
    1055                1060                1065

Ile Lys  Tyr Phe Asn Leu Phe  Asp Lys Glu Leu Asn  Glu Lys Glu
    1070                1075                1080

Ile Lys  Asp Leu Tyr Asp Asn  Gln Ser Asn Ser Gly  Ile Leu Lys
    1085                1090                1095

Asp Phe  Trp Gly Asp Tyr Leu  Gln Tyr Asp Lys Pro  Tyr Tyr Met
    1100                1105                1110

Leu Asn  Leu Tyr Asp Pro Asn  Lys Tyr Val Asp Val  Asn Asn Val
    1115                1120                1125

Gly Ile  Arg Gly Tyr Met Tyr  Leu Lys Gly Pro Arg  Gly Ser Val
    1130                1135                1140

Met Thr  Thr Asn Ile Tyr Leu  Asn Ser Ser Leu Tyr  Arg Gly Thr
    1145                1150                1155

Lys Phe  Ile Ile Lys Lys Tyr  Ala Ser Gly Asn Lys  Asp Asn Ile
    1160                1165                1170

Val Arg  Asn Asn Asp Arg Val  Tyr Ile Asn Val Val  Val Lys Asn
    1175                1180                1185
```

```
Lys Glu  Tyr Arg Leu Ala Thr  Asn Ala Ser Gln Ala  Gly Val Glu
    1190                 1195                 1200

Lys Ile  Leu Ser Ala Leu Glu  Ile Pro Asp Val Gly  Asn Leu Ser
    1205                 1210                 1215

Gln Val  Val Val Met Lys Ser  Lys Asn Asp Gln Gly  Ile Thr Asn
    1220                 1225                 1230

Lys Cys  Lys Met Asn Leu Gln  Asp Asn Asn Gly Asn  Asp Ile Gly
    1235                 1240                 1245

Phe Ile  Gly Phe His Gln Phe  Asn Asn Ile Ala Lys  Leu Val Ala
    1250                 1255                 1260

Ser Asn  Trp Tyr Asn Arg Gln  Ile Glu Arg Ser Ser  Arg Thr Leu
    1265                 1270                 1275

Gly Cys  Ser Trp Glu Phe Ile  Pro Val Asp Asp Gly  Trp Gly Glu
    1280                 1285                 1290

Arg Pro  Leu
    1295
```

<210> SEQ ID NO 3
<211> LENGTH: 3876
<212> TYPE: DNA
<213> ORGANISM: Clostridium botulinum

<400> SEQUENCE: 3

```
atgccagtta caataaataa ttttaattat aatgatccta ttgataataa taatattatt     60

atgatggagc ctccatttgc gagaggtacg gggagatatt ataaagcttt taaaatcaca    120

gatcgtattt ggataatacc ggaaagatat acttttggat ataaacctga ggattttaat    180

aaaagttccg gtatttttaa tagagatgtt tgtgaatatt atgatccaga ttacttaaat    240

actaatgata aaaagaatat atttttacaa acaatgatca agttatttaa tagaatcaaa    300

tcaaaaccat tgggtgaaaa gttattagag atgattataa atggtatacc ttatcttgga    360

gatagacgtg ttccactcga agagtttaac acaaacattg ctagtgtaac tgttaataaa    420

ttaatcagta atccaggaga agtggagcga aaaaaaggta ttttcgcaaa tttaataata    480

tttggacctg ggccagtttt aaatgaaaat gagactatag atataggtat acaaaatcat    540

tttgcatcaa gggaaggctt cgggggtata atgcaaatga agttttgccc agaatatgta    600

agcgtattta ataatgttca agaaaacaaa ggcgcaagta tatttaatag acgtggatat    660

ttttcagatc cagccttgat attaatgcat gaacttatac atgttttaca tggattatat    720

ggcattaaag tagatgattt accaattgta ccaaatgaaa aaaaattttt tatgcaatct    780

acagatgcta tacaggcaga agaactatat acatttggag gacaagatcc cagcatcata    840

actccttcta cggataaaag tatctatgat aaagttttgc aaaattttag agggatagtt    900

gatagactta acaaggtttt agtttgcata tcagatccta acattaatat taatatatat    960

aaaaataaat ttaaagataa atataaattc gttgaagatt ctgagggaaa atatagtata   1020

gatgtagaaa gttttgataa attatataaa agcttaatgt ttggttttac agaaactaat   1080

atagcagaaa attataaaat aaaaactaga gcttcttatt ttagtgattc cttaccacca   1140

gtaaaaataa aaaatttatt agataatgaa atctatacta tagaggaagg gtttaatata   1200

tctgataaag atatggaaaa agaatataga ggtcagaata aagctataaa taaacaagct   1260

tatgaagaaa ttagcaagga gcatttggct gtatataaga tacaaatgtg taaaagtgtt   1320

aaagctccag gaatatgtat tgatgttgat aatgaagatt tgttctttat agctgataaa   1380
```

```
aatagttttt cagatgattt atctaaaaac gaaagaatag aatataatac acagagtaat   1440

tatatagaaa atgacttccc tataaatgaa ttaattttag atactgattt aataagtaaa   1500

atagaattac caagtgaaaa tacagaatca cttactgatt ttaatgtaga tgttccagta   1560

tatgaaaaac aacccgctat aaaaaaaatt tttacagatg aaaataccat ctttcaatat   1620

ttatactctc agacatttcc tctagatata agagatataa gtttaacatc ttcatttgat   1680

gatgcattat tattttctaa caaagtttat tcattttttt ctatggatta tattaaaact   1740

gctaataaag tggtagaagc aggattattt gcaggttggg tgaaacagat agtaaatgat   1800

tttgtaatcg aagctaataa aagcaatact atggataaaa ttgcagatat atctctaatt   1860

gttccttata taggattagc tttaaatgta ggaaatgaaa cagctaaagg aaattttgaa   1920

aatgcttttg agattgcagg agccagtatt ctactagaat ttataccaga acttttaata   1980

cctgtagttg gagccttttt attagaatca tatattgaca ataaaaataa aattattaaa   2040

acaatagata atgctttaac taaaagaaat gaaaaatgga gtgatatgta cggattaata   2100

gtagcgcaat ggctctcaac agttaatact caattttata caataaaaga gggaatgtat   2160

aaggctttaa attatcaagc acaagcattg gaagaaataa taaaatacag atataatata   2220

tattctgaaa aagaaaagtc aaatattaac atcgatttta atgatataaa ttctaaactt   2280

aatgagggta ttaaccaagc tatagataat ataaataatt ttataaatgg atgttctgta   2340

tcatatttaa tgaaaaaaat gattccatta gctgtagaaa aattactaga ctttgataat   2400

actctcaaaa aaaatttgtt aaattatata gatgaaaata aattatattt gattggaagt   2460

gcagaatatg aaaaatcaaa agtaaataaa tacttgaaaa ccattatgcc gtttgatctt   2520

tcaatatata ccaatgatac aatactaata gaaatgttta ataaatataa tagcgaaatt   2580

ttaaataata ttatcttaaa tttaagatat aaggataata atttaataga tttatcagga   2640

tatggggcaa aggtagaggt atatgatgga gtcgagctta atgataaaaa tcaatttaaa   2700

ttaactagtt cagcaaatag taagattaga gtgactcaaa atcagaatat catatttaat   2760

agtgtgttcc ttgattttag cgttagcttt tggataagaa tacctaaata taagaatgat   2820

ggtatacaaa attatattca taatgaatat acaataatta attgtatgaa aaataattcg   2880

ggctggaaaa tatctattag ggtaatagg ataatatgga ctttaattga tataaatgga   2940

aaaaccaaat cggtattttt tgaatataac ataagagaag atatatcaga gtatataaat   3000

agatggtttt ttgtaactat tactaataat ttgaataacg ctaaaattta tattaatggt   3060

aagctagaat caaatacaga tattaaagat ataagagaag ttattgctaa tggtgaaata   3120

atatttaaat tagatggtga tatagataga acacaattta tttggatgaa atatttcagt   3180

atttttaata cggaattaag tcaatcaaat attgaagaaa gatataaaat tcaatcatat   3240

agcgaatatt taaaagattt ttggggaaat cctttaatgt acaataaaga atattatatg   3300

tttaatgcgg ggaataaaaa ttcatatatt aaactaaaga aagattcacc tgtaggtgaa   3360

attttaacac gtagcaaata taatcaaaat tctaaatata taaattatag agatttatat   3420

attggagaaa aatttattat aagaagaaag tcaaattctc aatctataaa tgatgatata   3480

gttagaaaag aagattatat atatctagat ttttttaatt taaatcaaga gtggagagta   3540

tatacctata aatattttaa gaaagaggaa gaaaaattgt ttttagctcc tataagtgat   3600

tctgatgagt tttacaatac tatacaaata aaagaatatg atgaacagcc aacatatagt   3660

tgtcagttgc tttttaaaaa agatgaagaa agtactgatg agataggatt gattggtatt   3720

catcgtttct acgaatctgg aattgtattt gaagagtata aagattattt ttgtataagt   3780
```

```
aaatggtact taaaagaggt aaaaaggaaa ccatataatt taaaattggg atgtaattgg   3840

cagtttattc ctaaagatga agggtggact gaataa                             3876


<210> SEQ ID NO 4
<211> LENGTH: 1291
<212> TYPE: PRT
<213> ORGANISM: Clostridium botulinum

<400> SEQUENCE: 4

Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
        275                 280                 285

Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350
```

```
Met Phe Gly Phe Thr Glu Thr Asn Ile Ala Glu Asn Tyr Lys Ile Lys
        355                 360                 365

Thr Arg Ala Ser Tyr Phe Ser Asp Ser Leu Pro Pro Val Lys Ile Lys
    370                 375                 380

Asn Leu Leu Asp Asn Glu Ile Tyr Thr Ile Glu Glu Gly Phe Asn Ile
385                 390                 395                 400

Ser Asp Lys Asp Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Lys Ala Pro Gly Ile Cys Ile Asp
        435                 440                 445

Val Asp Asn Glu Asp Leu Phe Phe Ile Ala Asp Lys Asn Ser Phe Ser
    450                 455                 460

Asp Asp Leu Ser Lys Asn Glu Arg Ile Glu Tyr Asn Thr Gln Ser Asn
465                 470                 475                 480

Tyr Ile Glu Asn Asp Phe Pro Ile Asn Glu Leu Ile Leu Asp Thr Asp
                485                 490                 495

Leu Ile Ser Lys Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
        515                 520                 525

Lys Ile Phe Thr Asp Glu Asn Thr Ile Phe Gln Tyr Leu Tyr Ser Gln
    530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Phe Ser Met Asp
                565                 570                 575

Tyr Ile Lys Thr Ala Asn Lys Val Val Glu Ala Gly Leu Phe Ala Gly
            580                 585                 590

Trp Val Lys Gln Ile Val Asn Asp Phe Val Ile Glu Ala Asn Lys Ser
        595                 600                 605

Asn Thr Met Asp Lys Ile Ala Asp Ile Ser Leu Ile Val Pro Tyr Ile
    610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655

Glu Leu Leu Ile Pro Val Val Gly Ala Phe Leu Leu Glu Ser Tyr Ile
            660                 665                 670

Asp Asn Lys Asn Lys Ile Ile Lys Thr Ile Asp Asn Ala Leu Thr Lys
        675                 680                 685

Arg Asn Glu Lys Trp Ser Asp Met Tyr Gly Leu Ile Val Ala Gln Trp
    690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735

Arg Tyr Asn Ile Tyr Ser Glu Lys Glu Lys Ser Asn Ile Asn Ile Asp
            740                 745                 750

Phe Asn Asp Ile Asn Ser Lys Leu Asn Glu Gly Ile Asn Gln Ala Ile
        755                 760                 765

Asp Asn Ile Asn Asn Phe Ile Asn Gly Cys Ser Val Ser Tyr Leu Met
```

```
    770                 775                 780

Lys Lys Met Ile Pro Leu Ala Val Glu Lys Leu Leu Asp Phe Asp Asn
785                 790                 795                 800

Thr Leu Lys Lys Asn Leu Leu Asn Tyr Ile Asp Glu Asn Lys Leu Tyr
                805                 810                 815

Leu Ile Gly Ser Ala Glu Tyr Glu Lys Ser Lys Val Asn Lys Tyr Leu
            820                 825                 830

Lys Thr Ile Met Pro Phe Asp Leu Ser Ile Tyr Thr Asn Asp Thr Ile
        835                 840                 845

Leu Ile Glu Met Phe Asn Lys Tyr Asn Ser Glu Ile Leu Asn Asn Ile
    850                 855                 860

Ile Leu Asn Leu Arg Tyr Lys Asp Asn Asn Leu Ile Asp Leu Ser Gly
865                 870                 875                 880

Tyr Gly Ala Lys Val Glu Val Tyr Asp Gly Val Glu Leu Asn Asp Lys
                885                 890                 895

Asn Gln Phe Lys Leu Thr Ser Ser Ala Asn Ser Lys Ile Arg Val Thr
            900                 905                 910

Gln Asn Gln Asn Ile Ile Phe Asn Ser Val Phe Leu Asp Phe Ser Val
        915                 920                 925

Ser Phe Trp Ile Arg Ile Pro Lys Tyr Lys Asn Asp Gly Ile Gln Asn
    930                 935                 940

Tyr Ile His Asn Glu Tyr Thr Ile Ile Asn Cys Met Lys Asn Asn Ser
945                 950                 955                 960

Gly Trp Lys Ile Ser Ile Arg Gly Asn Arg Ile Ile Trp Thr Leu Ile
                965                 970                 975

Asp Ile Asn Gly Lys Thr Lys Ser Val Phe Phe Glu Tyr Asn Ile Arg
            980                 985                 990

Glu Asp Ile Ser Glu Tyr Ile Asn  Arg Trp Phe Phe Val  Thr Ile Thr
        995                 1000                1005

Asn Asn  Leu Asn Asn Ala Lys  Ile Tyr Ile Asn Gly  Lys Leu Glu
    1010                1015                1020

Ser Asn  Thr Asp Ile Lys Asp  Ile Arg Glu Val Ile  Ala Asn Gly
    1025                1030                1035

Glu Ile  Ile Phe Lys Leu Asp  Gly Asp Ile Asp Arg  Thr Gln Phe
    1040                1045                1050

Ile Trp  Met Lys Tyr Phe Ser  Ile Phe Asn Thr Glu  Leu Ser Gln
    1055                1060                1065

Ser Asn  Ile Glu Glu Arg Tyr  Lys Ile Gln Ser Tyr  Ser Glu Tyr
    1070                1075                1080

Leu Lys  Asp Phe Trp Gly Asn  Pro Leu Met Tyr Asn  Lys Glu Tyr
    1085                1090                1095

Tyr Met  Phe Asn Ala Gly Asn  Lys Asn Ser Tyr Ile  Lys Leu Lys
    1100                1105                1110

Lys Asp  Ser Pro Val Gly Glu  Ile Leu Thr Arg Ser  Lys Tyr Asn
    1115                1120                1125

Gln Asn  Ser Lys Tyr Ile Asn  Tyr Arg Asp Leu Tyr  Ile Gly Glu
    1130                1135                1140

Lys Phe  Ile Ile Arg Arg Lys  Ser Asn Ser Gln Ser  Ile Asn Asp
    1145                1150                1155

Asp Ile  Val Arg Lys Glu Asp  Tyr Ile Tyr Leu Asp  Phe Phe Asn
    1160                1165                1170

Leu Asn  Gln Glu Trp Arg Val  Tyr Thr Tyr Lys Tyr  Phe Lys Lys
    1175                1180                1185
```

```
Glu Glu  Glu Lys Leu Phe Leu  Ala Pro Ile Ser Asp  Ser Asp Glu
    1190                 1195                 1200

Phe Tyr  Asn Thr Ile Gln Ile  Lys Glu Tyr Asp Glu  Gln Pro Thr
    1205                 1210                 1215

Tyr Ser  Cys Gln Leu Leu Phe  Lys Lys Asp Glu Glu  Ser Thr Asp
    1220                 1225                 1230

Glu Ile  Gly Leu Ile Gly Ile  His Arg Phe Tyr Glu  Ser Gly Ile
    1235                 1240                 1245

Val Phe  Glu Glu Tyr Lys Asp  Tyr Phe Cys Ile Ser  Lys Trp Tyr
    1250                 1255                 1260

Leu Lys  Glu Val Lys Arg Lys  Pro Tyr Asn Leu Lys  Leu Gly Cys
    1265                 1270                 1275

Asn Trp  Gln Phe Ile Pro Lys  Asp Glu Gly Trp Thr  Glu
    1280                 1285                 1290


<210> SEQ ID NO 5
<211> LENGTH: 3843
<212> TYPE: DNA
<213> ORGANISM: Clostridium botulinum

<400> SEQUENCE: 5

atgccaataa caattaacaa ctttaattat tcagatcctg ttgataataa aaatatttta     60

tatttagata ctcatttaaa tacattagct aatgagcctg aaaaagcctt tcgcattata    120

gggaatatat gggtaatacc cgatagattt tcaagagatt ctaatccaaa tttaaataaa    180

cctcctcgag ttacaagccc taaaagtggt tattatgatc ctaattattt gagtactgat    240

tctgaaaaag atacattttt aaaagaaatt ataaagttat ttaaaagaat taactctaga    300

gaaataggag aagaattaat atatagactt gcaacagaca taccctttcc tgggaataac    360

aatactccaa ttaatacttt tgattttgat gtagatttta acagtgttga tgttaaaact    420

agacaaggta acaactgggt taaaactggt agtataaatc ctagtgttat aataactgga    480

cctagagaaa acattataga cccagaaact tctacgttta aattaactaa caatactttt    540

gcggcacaag aaggatttgg tgctttatca ataatttcaa tatcacctag atttatgcta    600

acatatagta atgcaactaa taatgtagga gagggtagat ttctaagtc tgaattttgc    660

atggatccaa tactaatttt aatgcatgaa cttaatcatg caatgcataa tttatatgga    720

atagctatac caaatgatca aagaatttca tctgtaacta gtaatatttt ttattctcaa    780

tataaggtga aattagagta tgcagaaata tatgcatttg gaggtccaac tatagacctt    840

attcctaaaa gtgcaaggaa atattttgag gaaaaggcat tggattatta tagatccata    900

gctaaaagac ttaatagtat aactactgca aatccttcaa gctttaataa atatatagga    960

gaatataaac agaaacttat tagaaagtat agattcgtag tagaatcttc aggtgaagtt   1020

gcagtagatc gtaataagtt tgctgagtta tataaagaac ttacacaaat atttacagaa   1080

tttaactacg ctaaaatata taatgtacaa aataggaaaa tatatctttc aaatgtatat   1140

actccggtta cggcaaatat attagacgat aatgtttatg atatacaaaa tggatttaac   1200

atacctaaaa gtaatttaaa tgtactattt atgggtcaaa atttatctcg aaatccagca   1260

ttaagaaaag tcaatcctga aaatatgctt tatttattta caaaattttg ccataaagca   1320

atagatggta gatcattata taataaaaca ttagattgta gagagctttt agttaaaaat   1380

actgacttac cctttatagg tgatattagt gatatcaaaa ctgatatatt tttaagcaaa   1440

gatattaatg aagaaactga agttatagac tatccggaca atgtttcagt ggatcaagtt   1500
```

```
attctcagta agaatacctc agaacatgga caactagatt tattataccc tattattgaa   1560
ggtgagagtc aagtattacc gggagagaat caagtctttt atgataatag aactcaaaat   1620
gttgattatt tgaattctta ttattaccta gaatctcaaa aactaagtga taatgttgaa   1680
gattttactt ttacgacatc aattgaggaa gctttggata atagtggaaa agtatatact   1740
tactttccta aactagctga taaagtaaat acgggtgttc aaggtggttt atttttaatg   1800
tgggcaaatg atgtagttga agattttact acaaatattc taagaaaaga tacattagat   1860
aaaatatcag atgtatcagc tattattccc tatataggac ctgcattaaa tataagtaat   1920
tctgtaagaa ggggaaattt tactgaagca tttgcagtta ccggtgtaac tattttatta   1980
gaagcgtttc aagaatttac aatacctgca cttggtgcat ttgtgattta tagtaaggtt   2040
caagaaagaa acgagattat taaaactata gataattgtt tagaacaaag gattaaaaga   2100
tggaaagatt catatgaatg gatgatagga acgtggttat ccaggattac tactcaattt   2160
aataatataa gttatcaaat gtatgattct ttaaattatc aggcagatgc aatcaaagat   2220
aaaatagatt tagaatataa aaaatactca ggaagtgata aagaaaatat aaaaagtcaa   2280
gttgaaaatt taaaaaatag tttagatata aaaatctcgg aagcaatgaa taatataaat   2340
aaatttatac gagaatgttc tgtaacatac ttatttaaaa atatgctccc taaagtaatt   2400
gatgaattaa ataagtttga tttaaaaact aaaacagaat taattaatct tatagatagt   2460
cataatatta ttctagttgg tgaagtagat agattaaaag caaaagtaaa tgagagtttt   2520
gaaaatacaa taccctttaa tattttttca tatactaata attctttatt aaaagatata   2580
attaatgaat atttcaatag tattaatgat tcaaaaattt tgagcttaca aaacaaaaaa   2640
aatgctttag tggatacatc aggatataat gcagaagtga ggctagaagg tgatgttcaa   2700
gttaatacga tatatacaaa tgattttaaa ttaagtagtt caggagataa aattatagta   2760
aatttaaata ataatatttt atatagcgct atttatgaga actctagtgt tagtttttgg   2820
attaagatat ctaaagattt aactaattct cataatgaat atacaataat taatagtata   2880
aaacaaaatt ctgggtggaa attatgtatt aggaatggca atatagaatg gattttacaa   2940
gatattaata gaaagtataa aagtttaatt tttgattata gtgaatcatt aagtcataca   3000
ggatatacaa ataaatggtt ttttgttact ataactaata atataatggg gtatatgaaa   3060
ctttatataa atggagaatt aaagcagagt gaaagaattg aagatttaaa tgaggttaag   3120
ttagataaaa ccatagtatt tggaatagat gagaatatag atgagaatca gatgctttgg   3180
attagagatt ttaatatttt ttctaaagaa ttaagcaatg aagatattaa tattgtatat   3240
gagggacaaa tattaagaaa tgttattaaa gattattggg gaaatccttt gaagtttgat   3300
acagaatatt atattattaa tgataattat atagataggt atatagcacc taaaagtaat   3360
atacttgtac ttgttcagta tccagataga tctaaattat atactggaaa tcctattact   3420
attaaatcag tatctgataa gaatccttat agtagaattt taaatggaga taatataatg   3480
tttcatatgt tatataatag tgggaaatat atgataataa gagatactga tacaatatat   3540
gcaatagaag gaagagagtg ttcaaaaaat tgtgtatatg cattaaaatt acagagtaat   3600
ttaggtaatt atggtatagg tatatttagt ataaaaaata ttgtatctca aaataaatat   3660
tgtagtcaaa ttttctctag ttttatgaaa aatacaatgc ttctagcaga tatatataaa   3720
ccttggagat tttcttttga aaatgcatac acgccagttg cagtaactaa ttatgagaca   3780
aaactattat caacttcatc tttttggaaa tttatttcta gggatccagg atgggtagag   3840
```

taa 3843

<210> SEQ ID NO 6
<211> LENGTH: 1280
<212> TYPE: PRT
<213> ORGANISM: Clostridium botulinum

<400> SEQUENCE: 6

```
Met Pro Ile Thr Ile Asn Asn Phe Asn Tyr Ser Asp Pro Val Asp Asn
1               5                   10                  15

Lys Asn Ile Leu Tyr Leu Asp Thr His Leu Asn Thr Leu Ala Asn Glu
            20                  25                  30

Pro Glu Lys Ala Phe Arg Ile Ile Gly Asn Ile Trp Val Ile Pro Asp
        35                  40                  45

Arg Phe Ser Arg Asp Ser Asn Pro Asn Leu Asn Lys Pro Pro Arg Val
    50                  55                  60

Thr Ser Pro Lys Ser Gly Tyr Tyr Asp Pro Asn Tyr Leu Ser Thr Asp
65                  70                  75                  80

Ser Glu Lys Asp Thr Phe Leu Lys Glu Ile Ile Lys Leu Phe Lys Arg
                85                  90                  95

Ile Asn Ser Arg Glu Ile Gly Glu Glu Leu Ile Tyr Arg Leu Ala Thr
            100                 105                 110

Asp Ile Pro Phe Pro Gly Asn Asn Asn Thr Pro Ile Asn Thr Phe Asp
        115                 120                 125

Phe Asp Val Asp Phe Asn Ser Val Asp Val Lys Thr Arg Gln Gly Asn
    130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asn
        195                 200                 205

Val Gly Glu Gly Arg Phe Ser Lys Ser Glu Phe Cys Met Asp Pro Ile
    210                 215                 220

Leu Ile Leu Met His Glu Leu Asn His Ala Met His Asn Leu Tyr Gly
225                 230                 235                 240

Ile Ala Ile Pro Asn Asp Gln Arg Ile Ser Ser Val Thr Ser Asn Ile
                245                 250                 255

Phe Tyr Ser Gln Tyr Lys Val Lys Leu Glu Tyr Ala Glu Ile Tyr Ala
            260                 265                 270

Phe Gly Gly Pro Thr Ile Asp Leu Ile Pro Lys Ser Ala Arg Lys Tyr
        275                 280                 285

Phe Glu Glu Lys Ala Leu Asp Tyr Tyr Arg Ser Ile Ala Lys Arg Leu
    290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
                325                 330                 335

Ser Gly Glu Val Ala Val Asp Arg Asn Lys Phe Ala Glu Leu Tyr Lys
            340                 345                 350

Glu Leu Thr Gln Ile Phe Thr Glu Phe Asn Tyr Ala Lys Ile Tyr Asn
        355                 360                 365
```

```
Val Gln Asn Arg Lys Ile Tyr Leu Ser Asn Val Tyr Thr Pro Val Thr
    370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
                405                 410                 415

Arg Asn Pro Ala Leu Arg Lys Val Asn Pro Glu Asn Met Leu Tyr Leu
            420                 425                 430

Phe Thr Lys Phe Cys His Lys Ala Ile Asp Gly Arg Ser Leu Tyr Asn
        435                 440                 445

Lys Thr Leu Asp Cys Arg Glu Leu Leu Val Lys Asn Thr Asp Leu Pro
    450                 455                 460

Phe Ile Gly Asp Ile Ser Asp Ile Lys Thr Asp Ile Phe Leu Ser Lys
465                 470                 475                 480

Asp Ile Asn Glu Glu Thr Glu Val Ile Asp Tyr Pro Asp Asn Val Ser
                485                 490                 495

Val Asp Gln Val Ile Leu Ser Lys Asn Thr Ser Glu His Gly Gln Leu
            500                 505                 510

Asp Leu Leu Tyr Pro Ile Ile Glu Gly Glu Ser Gln Val Leu Pro Gly
        515                 520                 525

Glu Asn Gln Val Phe Tyr Asp Asn Arg Thr Gln Asn Val Asp Tyr Leu
    530                 535                 540

Asn Ser Tyr Tyr Tyr Leu Glu Ser Gln Lys Leu Ser Asp Asn Val Glu
545                 550                 555                 560

Asp Phe Thr Phe Thr Thr Ser Ile Glu Glu Ala Leu Asp Asn Ser Gly
                565                 570                 575

Lys Val Tyr Thr Tyr Phe Pro Lys Leu Ala Asp Lys Val Asn Thr Gly
            580                 585                 590

Val Gln Gly Gly Leu Phe Leu Met Trp Ala Asn Asp Val Val Glu Asp
        595                 600                 605

Phe Thr Thr Asn Ile Leu Arg Lys Asp Thr Leu Asp Lys Ile Ser Asp
    610                 615                 620

Val Ser Ala Ile Ile Pro Tyr Ile Gly Pro Ala Leu Asn Ile Ser Asn
625                 630                 635                 640

Ser Val Arg Arg Gly Asn Phe Thr Glu Ala Phe Ala Val Thr Gly Val
                645                 650                 655

Thr Ile Leu Leu Glu Ala Phe Gln Glu Phe Thr Ile Pro Ala Leu Gly
            660                 665                 670

Ala Phe Val Ile Tyr Ser Lys Val Gln Glu Arg Asn Glu Ile Ile Lys
        675                 680                 685

Thr Ile Asp Asn Cys Leu Glu Gln Arg Ile Lys Arg Trp Lys Asp Ser
    690                 695                 700

Tyr Glu Trp Met Ile Gly Thr Trp Leu Ser Arg Ile Thr Thr Gln Phe
705                 710                 715                 720

Asn Asn Ile Ser Tyr Gln Met Tyr Asp Ser Leu Asn Tyr Gln Ala Asp
                725                 730                 735

Ala Ile Lys Asp Lys Ile Asp Leu Glu Tyr Lys Lys Tyr Ser Gly Ser
            740                 745                 750

Asp Lys Glu Asn Ile Lys Ser Gln Val Glu Asn Leu Lys Asn Ser Leu
        755                 760                 765

Asp Ile Lys Ile Ser Glu Ala Met Asn Asn Ile Asn Lys Phe Ile Arg
    770                 775                 780

Glu Cys Ser Val Thr Tyr Leu Phe Lys Asn Met Leu Pro Lys Val Ile
```

```
785                 790                 795                 800

Asp Glu Leu Asn Lys Phe Asp Leu Lys Thr Lys Thr Glu Leu Ile Asn
                805                 810                 815

Leu Ile Asp Ser His Asn Ile Ile Leu Val Gly Glu Val Asp Arg Leu
            820                 825                 830

Lys Ala Lys Val Asn Glu Ser Phe Glu Asn Thr Ile Pro Phe Asn Ile
        835                 840                 845

Phe Ser Tyr Thr Asn Asn Ser Leu Leu Lys Asp Ile Ile Asn Glu Tyr
    850                 855                 860

Phe Asn Ser Ile Asn Asp Ser Lys Ile Leu Ser Leu Gln Asn Lys Lys
865                 870                 875                 880

Asn Ala Leu Val Asp Thr Ser Gly Tyr Asn Ala Glu Val Arg Leu Glu
                885                 890                 895

Gly Asp Val Gln Val Asn Thr Ile Tyr Thr Asn Asp Phe Lys Leu Ser
            900                 905                 910

Ser Ser Gly Asp Lys Ile Ile Val Asn Leu Asn Asn Asn Ile Leu Tyr
        915                 920                 925

Ser Ala Ile Tyr Glu Asn Ser Ser Val Ser Phe Trp Ile Lys Ile Ser
    930                 935                 940

Lys Asp Leu Thr Asn Ser His Asn Glu Tyr Thr Ile Ile Asn Ser Ile
945                 950                 955                 960

Lys Gln Asn Ser Gly Trp Lys Leu Cys Ile Arg Asn Gly Asn Ile Glu
                965                 970                 975

Trp Ile Leu Gln Asp Ile Asn Arg Lys Tyr Lys Ser Leu Ile Phe Asp
            980                 985                 990

Tyr Ser Glu Ser Leu Ser His Thr  Gly Tyr Thr Asn Lys  Trp Phe Phe
        995                 1000                1005

Val Thr  Ile Thr Asn Asn Ile  Met Gly Tyr Met Lys  Leu Tyr Ile
    1010                1015                1020

Asn Gly  Glu Leu Lys Gln Ser  Glu Arg Ile Glu Asp  Leu Asn Glu
    1025                1030                1035

Val Lys  Leu Asp Lys Thr Ile  Val Phe Gly Ile Asp  Glu Asn Ile
    1040                1045                1050

Asp Glu  Asn Gln Met Leu Trp  Ile Arg Asp Phe Asn  Ile Phe Ser
    1055                1060                1065

Lys Glu  Leu Ser Asn Glu Asp  Ile Asn Ile Val Tyr  Glu Gly Gln
    1070                1075                1080

Ile Leu  Arg Asn Val Ile Lys  Asp Tyr Trp Gly Asn  Pro Leu Lys
    1085                1090                1095

Phe Asp  Thr Glu Tyr Tyr Ile  Ile Asn Asp Asn Tyr  Ile Asp Arg
    1100                1105                1110

Tyr Ile  Ala Pro Lys Ser Asn  Ile Leu Val Leu Val  Gln Tyr Pro
    1115                1120                1125

Asp Arg  Ser Lys Leu Tyr Thr  Gly Asn Pro Ile Thr  Ile Lys Ser
    1130                1135                1140

Val Ser  Asp Lys Asn Pro Tyr  Ser Arg Ile Leu Asn  Gly Asp Asn
    1145                1150                1155

Ile Met  Phe His Met Leu Tyr  Asn Ser Gly Lys Tyr  Met Ile Ile
    1160                1165                1170

Arg Asp  Thr Asp Thr Ile Tyr  Ala Ile Glu Gly Arg  Glu Cys Ser
    1175                1180                1185

Lys Asn  Cys Val Tyr Ala Leu  Lys Leu Gln Ser Asn  Leu Gly Asn
    1190                1195                1200
```

```
Tyr Gly  Ile Gly Ile Phe Ser  Ile Lys Asn Ile Val  Ser Gln Asn
    1205                 1210                 1215

Lys Tyr  Cys Ser Gln Ile Phe  Ser Ser Phe Met Lys  Asn Thr Met
    1220                 1225                 1230

Leu Leu  Ala Asp Ile Tyr Lys  Pro Trp Arg Phe Ser  Phe Glu Asn
    1235                 1240                 1245

Ala Tyr  Thr Pro Val Ala Val  Thr Asn Tyr Glu Thr  Lys Leu Leu
    1250                 1255                 1260

Ser Thr  Ser Ser Phe Trp Lys  Phe Ile Ser Arg Asp  Pro Gly Trp
    1265                 1270                 1275

Val Glu
    1280


<210> SEQ ID NO 7
<211> LENGTH: 3858
<212> TYPE: DNA
<213> ORGANISM: Clostridium botulinum

<400> SEQUENCE: 7

atgacatggc cagtaaaaga ttttaattat agtgatcctg ttaatgacaa tgatatatta     60

tatttaagaa taccacaaaa taagttaatt actacacctg taaaagcttt tatgattact    120

caaaatattt gggtaatacc agaaagattt tcatcagata ctaatccaag tttaagtaaa    180

ccgcctagac ctacttcaaa gtatcaaagt tattatgatc ctagttattt atctactgat    240

gagcaaaaag atacattttt aaaagggatt ataaaattat ttaaaagaat taatgaaaga    300

gatataggaa aaaaattaat aaattattta gtagttggtt cacctttttat gggagattca    360

agtacgcctg aagatacatt tgattttaca cgtcatacta ctaatattgc agttgaaaag    420

tttgaaaatg gtagttggaa agtaacaaat attataacac caagtgtatt gatatttgga    480

ccacttccta atatattaga ctatacagca tcccttacat tgcaaggaca acaatcaaat    540

ccatcatttg aagggtttgg aacattatct atactaaaag tagcacctga atttttgtta    600

acatttagtg atgtaacatc taatcaaagt tcagctgtat taggcaaatc tatattttgt    660

atggatccag taatagcttt aatgcatgag ttaacacatt ctttgcatca attgtatgga    720

ataaatatac catctgataa aaggattcgt ccacaagtta gcgagggatt tttttctcaa    780

gatggaccca acgtacaatt tgaggaatta tacacatttg gaggatcaga tgttgaaata    840

atacctcaaa ttgaaagatt acaattaaga gaaaaagcat taggtcacta taaagatata    900

gcgaaaagac ttaataatat taataaaact attccttcta gttggagtag taatatagat    960

aaatataaaa aaatattttc tgaaaagtat aattttgata aagataatac aggaaatttt   1020

gttgtaaata ttgataaatt caatagctta tattcagact tgactaatgt tatgtcagaa   1080

gttgtttatt cttcgcaata taatgttaaa aacaggactc attatttttc aaagcattat   1140

ctacctgtat ttgcaaatat attagatgat aatatttata ctataataaa cggttttaat   1200

ttaacaacta aaggttttaa tatagaaaat tcgggtcaga atatagaaag gaatcctgca   1260

ctacaaaaac ttagttcaga aagtgtagta gatttgttta caaaagtatg tttaagatta   1320

acaagaaata gtagagatga ttcaacatgt attcaagtta aaaataatac attaccttat   1380

gtagctgata aagatagcat ttcacaagaa atatttgaaa gtcaaattat tacagatgag   1440

actaatgtag aaaattattc agataatttt tcattagatg aatctatttt agatgcaaaa   1500

gtccctacta atcctgaagc agtagatcca ctgttaccca atgttaatat ggaaccttta   1560
```

-continued

```
aatgttccag gtgaagaaga agtattttat gatgatatta ctaaagatgt tgattattta   1620
aactcttatt attatttgga agcccaaaaa ttaagtaata atgttgaaaa tattactctt   1680
acaacttcag ttgaagaagc attaggttat agcaataaga tatacacatt tttacctagc   1740
ttagctgaaa aagtgaataa aggtgttcaa gcaggtttat tcttaaattg ggcgaatgaa   1800
gtagttgagg attttactac aaatattatg aaaaaagata cattggataa aatatcagat   1860
gtatcagcca taattccata tataggacct gccttaaata taggaaattc agcattaagg   1920
ggaaacttta agcaagcatt tgcaacagct ggtgtagctt ttttgttaga aggatttcca   1980
gagtttacaa tacctgcact cggtgtattt accttttata gttctattca agaaagagag   2040
aaaattatta aaactataga aaattgttta gaacaaagag ttaagagatg gaaagattca   2100
tatcaatgga tggtatcaaa ttggttgtca agaattacta ctcgatttaa tcatataagt   2160
tatcaaatgt atgattcttt gagttatcag gcagatgcaa tcaaagctaa aatagattta   2220
gaatataaaa aatactcagg aagtgataaa gaaaatataa aaagtcaagt tgaaaattta   2280
aaaaatagtt tagatgtaaa aatctcggaa gcaatgaata atataaataa atttatacga   2340
gaatgttctg taacatactt atttaaaaat atgctcccta aagtaattga tgaattaaat   2400
aagtttgatt taaaaactaa aacagaatta attaatctta tagatagtca taatattatt   2460
ctagttggtg aagtagatag attaaaagca aaagtaaatg agagttttga aaatacaata   2520
ccctttaata ttttttcata tactaataat tctttattaa aagatatgat taatgaatat   2580
ttcaatagta ttaatgattc aaaaattttg agcttacaaa ataaaaaaaa tactttgatg   2640
gatacatcag gatataacgc agaagtgaga gtagaaggca atgttcagct taatccaata   2700
tttccatttg actttaaatt aggtagttca ggggatgata gaggtaaagt tatagtaacc   2760
cagaatgaaa atattgtata taatgctatg tatgaaagtt ttagtattag tttttggatt   2820
aggataaata aatgggtaag taatttacct ggatatacta taattgatag tgttaaaaat   2880
aactcaggtt ggagtatagg tattattagt aatttttttag tgtttacttt aaaacaaaat   2940
gaaaatagtg aacaagatat aaactttagt tatgatatat caaagaatgc tgcgggatat   3000
aataaatggt tttttgtaac tattactacc aatatgatgg gaaatatgat gatttatata   3060
aatggaaaat taatagatac tataaaagtt aaagagttaa ctggaattaa ttttagcaaa   3120
actataacat ttcaaatgaa taaaattcca aatactggct taattacctc agattctgat   3180
aacatcaata tgtggataag ggatttttat atctttgcta aagaattaga tgataaagat   3240
attaatatat tatttaatag cttgcaatat actaatgttg taaaagatta ttggggaaat   3300
gatttaagat atgataaaga atattacatg attaacgtaa attatatgaa tagatatatg   3360
tctaaaaaag gcaatggaat tgtttttaat acacgtaaaa ataataatga cttcaatgaa   3420
ggatataaaa ttataataaa aagaattaga ggaaatacaa atgatactag agtacgagga   3480
gaaaatgtat tatattttaa tactacaatt gataacaaac aatatagttt aggtatgtat   3540
aaaccttcta gaaatctagg gactgattta gttccactag gtgcattgga tcaaccaatg   3600
gatgagatac gtaaatatgg ttcgtttata atacaaccat gcaatacttt tgattactat   3660
gcatcacaat tatttttgtc aagtaatgca acaacaaata ggcttggaat actatcaatt   3720
ggtagttata gtttcaaact tggagatgac tattggttta atcacgaata tttaattcct   3780
gttataaaaa tagagcatta tgcttcatta ttagaatcaa catcaactca ttgggttttt   3840
gtacctgcaa gtgaataa                                                 3858
```

<210> SEQ ID NO 8
<211> LENGTH: 1285
<212> TYPE: PRT
<213> ORGANISM: Clostridium botulinum

<400> SEQUENCE: 8

Met Thr Trp Pro Val Lys Asp Phe Asn Tyr Ser Asp Pro Val Asn Asp
1 5 10 15

Asn Asp Ile Leu Tyr Leu Arg Ile Pro Gln Asn Lys Leu Ile Thr Thr
20 25 30

Pro Val Lys Ala Phe Met Ile Thr Gln Asn Ile Trp Val Ile Pro Glu
35 40 45

Arg Phe Ser Ser Asp Thr Asn Pro Ser Leu Ser Lys Pro Pro Arg Pro
50 55 60

Thr Ser Lys Tyr Gln Ser Tyr Tyr Asp Pro Ser Tyr Leu Ser Thr Asp
65 70 75 80

Glu Gln Lys Asp Thr Phe Leu Lys Gly Ile Ile Lys Leu Phe Lys Arg
85 90 95

Ile Asn Glu Arg Asp Ile Gly Lys Lys Leu Ile Asn Tyr Leu Val Val
100 105 110

Gly Ser Pro Phe Met Gly Asp Ser Ser Thr Pro Glu Asp Thr Phe Asp
115 120 125

Phe Thr Arg His Thr Thr Asn Ile Ala Val Glu Lys Phe Glu Asn Gly
130 135 140

Ser Trp Lys Val Thr Asn Ile Ile Thr Pro Ser Val Leu Ile Phe Gly
145 150 155 160

Pro Leu Pro Asn Ile Leu Asp Tyr Thr Ala Ser Leu Thr Leu Gln Gly
165 170 175

Gln Gln Ser Asn Pro Ser Phe Glu Gly Phe Gly Thr Leu Ser Ile Leu
180 185 190

Lys Val Ala Pro Glu Phe Leu Leu Thr Phe Ser Asp Val Thr Ser Asn
195 200 205

Gln Ser Ser Ala Val Leu Gly Lys Ser Ile Phe Cys Met Asp Pro Val
210 215 220

Ile Ala Leu Met His Glu Leu Thr His Ser Leu His Gln Leu Tyr Gly
225 230 235 240

Ile Asn Ile Pro Ser Asp Lys Arg Ile Arg Pro Gln Val Ser Glu Gly
245 250 255

Phe Phe Ser Gln Asp Gly Pro Asn Val Gln Phe Glu Glu Leu Tyr Thr
260 265 270

Phe Gly Gly Ser Asp Val Glu Ile Ile Pro Gln Ile Glu Arg Leu Gln
275 280 285

Leu Arg Glu Lys Ala Leu Gly His Tyr Lys Asp Ile Ala Lys Arg Leu
290 295 300

Asn Asn Ile Asn Lys Thr Ile Pro Ser Ser Trp Ser Ser Asn Ile Asp
305 310 315 320

Lys Tyr Lys Lys Ile Phe Ser Glu Lys Tyr Asn Phe Asp Lys Asp Asn
325 330 335

Thr Gly Asn Phe Val Val Asn Ile Asp Lys Phe Asn Ser Leu Tyr Ser
340 345 350

Asp Leu Thr Asn Val Met Ser Glu Val Val Tyr Ser Ser Gln Tyr Asn
355 360 365

Val Lys Asn Arg Thr His Tyr Phe Ser Lys His Tyr Leu Pro Val Phe
370 375 380

```
Ala Asn Ile Leu Asp Asp Asn Ile Tyr Thr Ile Ile Asn Gly Phe Asn
385                 390                 395                 400

Leu Thr Thr Lys Gly Phe Asn Ile Glu Asn Ser Gly Gln Asn Ile Glu
                405                 410                 415

Arg Asn Pro Ala Leu Gln Lys Leu Ser Ser Glu Ser Val Val Asp Leu
            420                 425                 430

Phe Thr Lys Val Cys Leu Arg Leu Thr Arg Asn Ser Arg Asp Asp Ser
        435                 440                 445

Thr Cys Ile Gln Val Lys Asn Asn Thr Leu Pro Tyr Val Ala Asp Lys
    450                 455                 460

Asp Ser Ile Ser Gln Glu Ile Phe Glu Ser Gln Ile Ile Thr Asp Glu
465                 470                 475                 480

Thr Asn Val Glu Asn Tyr Ser Asp Asn Phe Ser Leu Asp Glu Ser Ile
                485                 490                 495

Leu Asp Ala Lys Val Pro Thr Asn Pro Glu Ala Val Asp Pro Leu Leu
            500                 505                 510

Pro Asn Val Asn Met Glu Pro Leu Asn Val Pro Gly Glu Glu Glu Val
        515                 520                 525

Phe Tyr Asp Asp Ile Thr Lys Asp Val Asp Tyr Leu Asn Ser Tyr Tyr
    530                 535                 540

Tyr Leu Glu Ala Gln Lys Leu Ser Asn Asn Val Glu Asn Ile Thr Leu
545                 550                 555                 560

Thr Thr Ser Val Glu Glu Ala Leu Gly Tyr Ser Asn Lys Ile Tyr Thr
                565                 570                 575

Phe Leu Pro Ser Leu Ala Glu Lys Val Asn Lys Gly Val Gln Ala Gly
            580                 585                 590

Leu Phe Leu Asn Trp Ala Asn Glu Val Val Glu Asp Phe Thr Thr Asn
        595                 600                 605

Ile Met Lys Lys Asp Thr Leu Asp Lys Ile Ser Asp Val Ser Ala Ile
    610                 615                 620

Ile Pro Tyr Ile Gly Pro Ala Leu Asn Ile Gly Asn Ser Ala Leu Arg
625                 630                 635                 640

Gly Asn Phe Lys Gln Ala Phe Ala Thr Ala Gly Val Ala Phe Leu Leu
                645                 650                 655

Glu Gly Phe Pro Glu Phe Thr Ile Pro Ala Leu Gly Val Phe Thr Phe
            660                 665                 670

Tyr Ser Ser Ile Gln Glu Arg Glu Lys Ile Ile Lys Thr Ile Glu Asn
        675                 680                 685

Cys Leu Glu Gln Arg Val Lys Arg Trp Lys Asp Ser Tyr Gln Trp Met
    690                 695                 700

Val Ser Asn Trp Leu Ser Arg Ile Thr Thr Arg Phe Asn His Ile Ser
705                 710                 715                 720

Tyr Gln Met Tyr Asp Ser Leu Ser Tyr Gln Ala Asp Ala Ile Lys Ala
                725                 730                 735

Lys Ile Asp Leu Glu Tyr Lys Lys Tyr Ser Gly Ser Asp Lys Glu Asn
            740                 745                 750

Ile Lys Ser Gln Val Glu Asn Leu Lys Asn Ser Leu Asp Val Lys Ile
        755                 760                 765

Ser Glu Ala Met Asn Asn Ile Asn Lys Phe Ile Arg Glu Cys Ser Val
    770                 775                 780

Thr Tyr Leu Phe Lys Asn Met Leu Pro Lys Val Ile Asp Glu Leu Asn
785                 790                 795                 800

Lys Phe Asp Leu Lys Thr Lys Thr Glu Leu Ile Asn Leu Ile Asp Ser
```

```
                805                 810                 815

His Asn Ile Ile Leu Val Gly Glu Val Asp Arg Leu Lys Ala Lys Val
            820                 825                 830

Asn Glu Ser Phe Glu Asn Thr Ile Pro Phe Asn Ile Phe Ser Tyr Thr
        835                 840                 845

Asn Asn Ser Leu Leu Lys Asp Met Ile Asn Glu Tyr Phe Asn Ser Ile
    850                 855                 860

Asn Asp Ser Lys Ile Leu Ser Leu Gln Asn Lys Lys Asn Thr Leu Met
865                 870                 875                 880

Asp Thr Ser Gly Tyr Asn Ala Glu Val Arg Val Glu Gly Asn Val Gln
                885                 890                 895

Leu Asn Pro Ile Phe Pro Phe Asp Phe Lys Leu Gly Ser Ser Gly Asp
            900                 905                 910

Asp Arg Gly Lys Val Ile Val Thr Gln Asn Glu Asn Ile Val Tyr Asn
        915                 920                 925

Ala Met Tyr Glu Ser Phe Ser Ile Ser Phe Trp Ile Arg Ile Asn Lys
    930                 935                 940

Trp Val Ser Asn Leu Pro Gly Tyr Thr Ile Ile Asp Ser Val Lys Asn
945                 950                 955                 960

Asn Ser Gly Trp Ser Ile Gly Ile Ile Ser Asn Phe Leu Val Phe Thr
                965                 970                 975

Leu Lys Gln Asn Glu Asn Ser Glu Gln Asp Ile Asn Phe Ser Tyr Asp
            980                 985                 990

Ile Ser Lys Asn Ala Ala Gly Tyr  Asn Lys Trp Phe Phe  Val Thr Ile
        995                 1000                 1005

Thr Thr  Asn Met Met Gly Asn  Met Met Ile Tyr Ile  Asn Gly Lys
    1010                 1015                 1020

Leu Ile  Asp Thr Ile Lys Val  Lys Glu Leu Thr Gly  Ile Asn Phe
    1025                 1030                 1035

Ser Lys  Thr Ile Thr Phe Gln  Met Asn Lys Ile Pro  Asn Thr Gly
    1040                 1045                 1050

Leu Ile  Thr Ser Asp Ser Asp  Asn Ile Asn Met Trp  Ile Arg Asp
    1055                 1060                 1065

Phe Tyr  Ile Phe Ala Lys Glu  Leu Asp Asp Lys Asp  Ile Asn Ile
    1070                 1075                 1080

Leu Phe  Asn Ser Leu Gln Tyr  Thr Asn Val Val Lys  Asp Tyr Trp
    1085                 1090                 1095

Gly Asn  Asp Leu Arg Tyr Asp  Lys Glu Tyr Tyr Met  Ile Asn Val
    1100                 1105                 1110

Asn Tyr  Met Asn Arg Tyr Met  Ser Lys Lys Gly Asn  Gly Ile Val
    1115                 1120                 1125

Phe Asn  Thr Arg Lys Asn Asn  Asn Asp Phe Asn Glu  Gly Tyr Lys
    1130                 1135                 1140

Ile Ile  Ile Lys Arg Ile Arg  Gly Asn Thr Asn Asp  Thr Arg Val
    1145                 1150                 1155

Arg Gly  Glu Asn Val Leu Tyr  Phe Asn Thr Thr Ile  Asp Asn Lys
    1160                 1165                 1170

Gln Tyr  Ser Leu Gly Met Tyr  Lys Pro Ser Arg Asn  Leu Gly Thr
    1175                 1180                 1185

Asp Leu  Val Pro Leu Gly Ala  Leu Asp Gln Pro Met  Asp Glu Ile
    1190                 1195                 1200

Arg Lys  Tyr Gly Ser Phe Ile  Ile Gln Pro Cys Asn  Thr Phe Asp
    1205                 1210                 1215
```

```
Tyr Tyr Ala Ser Gln Leu Phe Leu Ser Ser Asn Ala Thr Thr Asn
    1220                1225                1230

Arg Leu Gly Ile Leu Ser Ile Gly Ser Tyr Ser Phe Lys Leu Gly
    1235                1240                1245

Asp Asp Tyr Trp Phe Asn His Glu Tyr Leu Ile Pro Val Ile Lys
    1250                1255                1260

Ile Glu His Tyr Ala Ser Leu Leu Glu Ser Thr Ser Thr His Trp
    1265                1270                1275

Val Phe Val Pro Ala Ser Glu
    1280                1285


<210> SEQ ID NO 9
<211> LENGTH: 3756
<212> TYPE: DNA
<213> ORGANISM: Clostridium botulinum

<400> SEQUENCE: 9

atgccaaaaa ttaatagttt taattataat gatcctgtta atgatagaac aattttatat     60

attaaaccag gcggttgtca agaattttat aaatcattta atattatgaa aaatatttgg    120

ataattccag agagaaatgt aattggtaca accccccaag attttcatcc gcctacttca    180

ttaaaaaatg gagatagtag ttattatgac cctaattatt tacaaagtga tgaagaaaag    240

gatagatttt taaaaatagt cacaaaaata tttaatagaa taaataataa tctttcagga    300

gggattttat tagaagaact gtcaaaagct aatccatatt tagggaatga taatactcca    360

gataatcaat tccatattgg tgatgcatca gcagttgaga ttaaattctc aaatggtagc    420

caagacatac tattacctaa tgttattata atgggagcag agcctgattt atttgaaact    480

aacagttcca atatttctct aagaaataat tatatgccaa gcaatcaccg ttttggatca    540

atagctatag taacattctc acctgaatat tcttttagat ttaatgataa ttgtatgaat    600

gaatttattc aagatcctgc tcttacatta atgcatgaat taatacattc attacatgga    660

ctatatgggg ctaaagggat tactacaaag tatactataa cacaaaaaca aaatccccta    720

ataacaaata taagaggtac aaatattgaa gaattcttaa cttttggagg tactgattta    780

aacattatta ctagtgctca gtccaatgat atctatacta atcttctagc tgattataaa    840

aaaatagcgt ctaaacttag caaagtacaa gtatctaatc cactacttaa tccttataaa    900

gatgtttttg aagcaaagta tggattagat aaagatgcta gcggaattta ttcggtaaat    960

ataaacaaat ttaatgatat ttttaaaaaa ttatacagct ttacggaatt tgatttacga   1020

actaaatttc aagttaaatg taggcaaact tatattggac agtataaata cttcaaactt   1080

tcaaacttgt taaatgattc tatttataat atatcagaag gctataatat aaataattta   1140

aaggtaaatt ttagaggaca gaatgcaaat ttaaatccta gaattattac accaattaca   1200

ggtagaggac tagtaaaaaa aatcattaga ttttgtaaaa atattgtttc tgtaaaaggc   1260

ataaggaaat caatatgtat cgaaataaat aatggtgagt tatttttttgt ggcttccgag   1320

aatagttata atgatgataa tataaatact cctaaagaaa ttgacgatac agtaacttca   1380

aataataatt atgaaaatga tttagatcag gttattttaa attttaatag tgaatcagca   1440

cctggacttt cagatgaaaa attaaattta actatccaaa atgatgctta tataccaaaa   1500

tatgattcta atggaacaag tgatatagaa caacatgatg ttaatgaact taatgtattt   1560

ttctatttag atgcacagaa agtgcccgaa ggtgaaaata atgtcaatct cacctcttca   1620

attgatacag cattattaga acaacctaaa atatatacat ttttttcatc agaatttatt   1680
```

```
aataatgtca ataaacctgt gcaagcagca ttatttgtaa gctggataca acaagtgtta   1740

gtagatttta ctactgaagc taaccaaaaa agtactgttg ataaaattgc agatatttct   1800

atagttgttc catatatagg tcttgcttta aatataggaa atgaagcaca aaaaggaaat   1860

tttaaagatg cacttgaatt attaggagca ggtattttat tagaatttga acccgagctt   1920

ttaattccta caattttagt attcacgata aaatcttttt taggttcatc tgataataaa   1980

aataaagtta ttaaagcaat aaataatgca ttgaaagaaa gagatgaaaa atggaaagaa   2040

gtatatagtt ttatagtatc gaattggatg actaaaatta atacacaatt taataaaaga   2100

aaagaacaaa tgtatcaagc tttacaaaat caagtaaatg caattaaaac aataatagaa   2160

tctaagtata atagttatac tttagaggaa aaaaatgagc ttacaaataa atatgatatt   2220

aagcaaatag aaaatgaact taatcaaaag gtttctatag caatgaataa tatagacagg   2280

ttcttaactg aaagttctat atcctattta atgaaaataa taaatgaagt aaaaattaat   2340

aaattaagag aatatgatga gaatgtcaaa acgtatttat tgaattatat tatacaacat   2400

ggatcaatct tgggagagag tcagcaagaa ctaaattcta tggtaactga taccctaaat   2460

aatagtattc cttttaagct ttcttcttat acagatgata aaattttaat ttcatatttt   2520

aataaattct ttaagagaat taaaagtagt tcagttttaa atatgagata taaaaatgat   2580

aaatacgtag atacttcagg atatgattca aatataaata ttaatggaga tgtatataaa   2640

tatccaacta ataaaaatca atttggaata tataatgata aacttagtga agttaatata   2700

tctcaaaatg attacattat atatgataat aaatataaaa attttagtat tagtttttgg   2760

gtaagaattc ctaactatga taataagata gtaaatgtta ataatgaata cactataata   2820

aattgtatga gagataataa ttcaggatgg aaagtatctc ttaatcataa tgaaataatt   2880

tggacattcg aagataatcg aggaattaat caaaaattag catttaacta tggtaacgca   2940

aatggtattt ctgattatat aaataagtgg atttttgtaa ctataactaa tgatagatta   3000

ggagattcta aactttatat taatggaaat ttaatagatc aaaaatcaat tttaaattta   3060

ggtaatattc atgttagtga caatatatta tttaaaatag ttaattgtag ttatacaaga   3120

tatattggta ttagatattt taatattttt gataaagaat tagatgaaac agaaattcaa   3180

actttatata gcaatgaacc taatacaaat attttgaagg atttttgggg aaattatttg   3240

ctttatgaca aagaatacta tttattaaat gtgttaaaac caaataactt tattgatagg   3300

agaaaagatt ctactttaag cattaataat ataagaagca ctattctttt agctaataga   3360

ttatatagtg gaataaaagt taaaatacaa agagttaata atagtagtac taacgataat   3420

cttgttagaa agaatgatca ggtatatatt aattttgtag ccagcaaaac tcacttattt   3480

ccattatatg ctgatacagc taccacaaat aaagagaaaa caataaaaat atcatcatct   3540

ggcaatagat ttaatcaagt agtagttatg aattcagtag gaaattgtac aatgaatttt   3600

aaaaataata atggaaataa tattgggttg ttaggtttca aggcagatac tgtcgttgct   3660

agtacttggt attatacaca tatgagagat catacaaaca gcaatggatg tttttggaac   3720

tttatttctg aagaacatgg atggcaagaa aaataa                              3756
```

<210> SEQ ID NO 10
<211> LENGTH: 1251
<212> TYPE: PRT
<213> ORGANISM: Clostridium botulinum

<400> SEQUENCE: 10

-continued

```
Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Arg Phe Gly Ser Ile Ala Ile Val Thr Phe Ser Pro Glu Tyr Ser Phe
            180                 185                 190

Arg Phe Asn Asp Asn Cys Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
    290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Arg Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
    370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Lys Asn Ile Val
                405                 410                 415

Ser Val Lys Gly Ile Arg Lys Ser Ile Cys Ile Glu Ile Asn Asn Gly
```

```
            420                 425                 430

Glu Leu Phe Phe Val Ala Ser Glu Asn Ser Tyr Asn Asp Asp Asn Ile
        435                 440                 445

Asn Thr Pro Lys Glu Ile Asp Asp Thr Val Thr Ser Asn Asn Asn Tyr
    450                 455                 460

Glu Asn Asp Leu Asp Gln Val Ile Leu Asn Phe Asn Ser Glu Ser Ala
465                 470                 475                 480

Pro Gly Leu Ser Asp Glu Lys Leu Asn Leu Thr Ile Gln Asn Asp Ala
                485                 490                 495

Tyr Ile Pro Lys Tyr Asp Ser Asn Gly Thr Ser Asp Ile Glu Gln His
            500                 505                 510

Asp Val Asn Glu Leu Asn Val Phe Phe Tyr Leu Asp Ala Gln Lys Val
        515                 520                 525

Pro Glu Gly Glu Asn Asn Val Asn Leu Thr Ser Ser Ile Asp Thr Ala
    530                 535                 540

Leu Leu Glu Gln Pro Lys Ile Tyr Thr Phe Phe Ser Ser Glu Phe Ile
545                 550                 555                 560

Asn Asn Val Asn Lys Pro Val Gln Ala Ala Leu Phe Val Ser Trp Ile
                565                 570                 575

Gln Gln Val Leu Val Asp Phe Thr Thr Glu Ala Asn Gln Lys Ser Thr
            580                 585                 590

Val Asp Lys Ile Ala Asp Ile Ser Ile Val Val Pro Tyr Ile Gly Leu
        595                 600                 605

Ala Leu Asn Ile Gly Asn Glu Ala Gln Lys Gly Asn Phe Lys Asp Ala
    610                 615                 620

Leu Glu Leu Leu Gly Ala Gly Ile Leu Leu Glu Phe Glu Pro Glu Leu
625                 630                 635                 640

Leu Ile Pro Thr Ile Leu Val Phe Thr Ile Lys Ser Phe Leu Gly Ser
                645                 650                 655

Ser Asp Asn Lys Asn Lys Val Ile Lys Ala Ile Asn Asn Ala Leu Lys
            660                 665                 670

Glu Arg Asp Glu Lys Trp Lys Glu Val Tyr Ser Phe Ile Val Ser Asn
        675                 680                 685

Trp Met Thr Lys Ile Asn Thr Gln Phe Asn Lys Arg Lys Glu Gln Met
    690                 695                 700

Tyr Gln Ala Leu Gln Asn Gln Val Asn Ala Ile Lys Thr Ile Ile Glu
705                 710                 715                 720

Ser Lys Tyr Asn Ser Tyr Thr Leu Glu Glu Lys Asn Glu Leu Thr Asn
                725                 730                 735

Lys Tyr Asp Ile Lys Gln Ile Glu Asn Glu Leu Asn Gln Lys Val Ser
            740                 745                 750

Ile Ala Met Asn Asn Ile Asp Arg Phe Leu Thr Glu Ser Ser Ile Ser
        755                 760                 765

Tyr Leu Met Lys Ile Ile Asn Glu Val Lys Ile Asn Lys Leu Arg Glu
    770                 775                 780

Tyr Asp Glu Asn Val Lys Thr Tyr Leu Leu Asn Tyr Ile Ile Gln His
785                 790                 795                 800

Gly Ser Ile Leu Gly Glu Ser Gln Gln Glu Leu Asn Ser Met Val Thr
                805                 810                 815

Asp Thr Leu Asn Asn Ser Ile Pro Phe Lys Leu Ser Ser Tyr Thr Asp
            820                 825                 830

Asp Lys Ile Leu Ile Ser Tyr Phe Asn Lys Phe Phe Lys Arg Ile Lys
        835                 840                 845
```

```
Ser Ser Ser Val Leu Asn Met Arg Tyr Lys Asn Asp Lys Tyr Val Asp
    850                 855                 860

Thr Ser Gly Tyr Asp Ser Asn Ile Asn Ile Asn Gly Asp Val Tyr Lys
865                 870                 875                 880

Tyr Pro Thr Asn Lys Asn Gln Phe Gly Ile Tyr Asn Asp Lys Leu Ser
                885                 890                 895

Glu Val Asn Ile Ser Gln Asn Asp Tyr Ile Ile Tyr Asp Asn Lys Tyr
            900                 905                 910

Lys Asn Phe Ser Ile Ser Phe Trp Val Arg Ile Pro Asn Tyr Asp Asn
        915                 920                 925

Lys Ile Val Asn Val Asn Asn Glu Tyr Thr Ile Ile Asn Cys Met Arg
    930                 935                 940

Asp Asn Asn Ser Gly Trp Lys Val Ser Leu Asn His Asn Glu Ile Ile
945                 950                 955                 960

Trp Thr Phe Glu Asp Asn Arg Gly Ile Asn Gln Lys Leu Ala Phe Asn
                965                 970                 975

Tyr Gly Asn Ala Asn Gly Ile Ser Asp Tyr Ile Asn Lys Trp Ile Phe
            980                 985                 990

Val Thr Ile Thr Asn Asp Arg Leu  Gly Asp Ser Lys Leu  Tyr Ile Asn
        995                 1000                1005

Gly Asn  Leu Ile Asp Gln Lys  Ser Ile Leu Asn Leu  Gly Asn Ile
    1010                1015                1020

His Val  Ser Asp Asn Ile Leu  Phe Lys Ile Val Asn  Cys Ser Tyr
    1025                1030                1035

Thr Arg  Tyr Ile Gly Ile Arg  Tyr Phe Asn Ile Phe  Asp Lys Glu
    1040                1045                1050

Leu Asp  Glu Thr Glu Ile Gln  Thr Leu Tyr Ser Asn  Glu Pro Asn
    1055                1060                1065

Thr Asn  Ile Leu Lys Asp Phe  Trp Gly Asn Tyr Leu  Leu Tyr Asp
    1070                1075                1080

Lys Glu  Tyr Tyr Leu Leu Asn  Val Leu Lys Pro Asn  Asn Phe Ile
    1085                1090                1095

Asp Arg  Arg Lys Asp Ser Thr  Leu Ser Ile Asn Asn  Ile Arg Ser
    1100                1105                1110

Thr Ile  Leu Leu Ala Asn Arg  Leu Tyr Ser Gly Ile  Lys Val Lys
    1115                1120                1125

Ile Gln  Arg Val Asn Asn Ser  Ser Thr Asn Asp Asn  Leu Val Arg
    1130                1135                1140

Lys Asn  Asp Gln Val Tyr Ile  Asn Phe Val Ala Ser  Lys Thr His
    1145                1150                1155

Leu Phe  Pro Leu Tyr Ala Asp  Thr Ala Thr Thr Asn  Lys Glu Lys
    1160                1165                1170

Thr Ile  Lys Ile Ser Ser Ser  Gly Asn Arg Phe Asn  Gln Val Val
    1175                1180                1185

Val Met  Asn Ser Val Gly Asn  Cys Thr Met Asn Phe  Lys Asn Asn
    1190                1195                1200

Asn Gly  Asn Asn Ile Gly Leu  Leu Gly Phe Lys Ala  Asp Thr Val
    1205                1210                1215

Val Ala  Ser Thr Trp Tyr Tyr  Thr His Met Arg Asp  His Thr Asn
    1220                1225                1230

Ser Asn  Gly Cys Phe Trp Asn  Phe Ile Ser Glu Glu  His Gly Trp
    1235                1240                1245
```

```
Gln Glu  Lys
    1250


<210> SEQ ID NO 11
<211> LENGTH: 3843
<212> TYPE: DNA
<213> ORGANISM: Clostridium botulinum

<400> SEQUENCE: 11

atgccagttg taataaatag ttttaattat aatgaccctg ttaatgatga gacaatttta     60

tacatgcaga aaccatatga agaaagaagt agaaaatatt ataaagcttt tgagattatg    120

cctaatgttt ggataatgcc tgagagagat acaataggaa ctaagcctga tgagtttcag    180

gtgccggatt cattaaagaa cggaagtagt gcttattatg atcctaatta tttaaccact    240

gatgctgaaa aagatagata tttaaaaaca atgataaaat tatttaatag aattaatagt    300

aatcctacag ggaaagtttt gttagaagaa gtatcaaatg ctagaccata tttaggagat    360

gatgacacgc taattaatga attccttcca gttaatgtaa ctacaagtgt taatataaaa    420

ttttcaactg atgttgaaag ttcaataata tcgaatcttc ttgtattggg agcaggacct    480

gatatattta aagcttactg tacccccctt gtaaggttta ataagtcaga taaattaatt    540

gaaccaagta atcatggttt tggatcaatt aatatcttga cattttcacc tgagtatgaa    600

catattttta atgatattag tggagggaat cataatagta cagaatcatt tattgcagat    660

cctgcaattt cactagctca tgaattgata catgcactac atggattata cggggctaag    720

gcagttactc ataaagagtc tctagtagca gagcgaggac ctcttatgat agccgaaaag    780

cccataaggc tagaagaatt tttaactttt ggaggtgagg atttaaatat cattcctagt    840

gctatgaagg aaaaaatata taacgatctt ttagctaact atgaaaaaat agctactaga    900

cttagagaag ttaatacggc tcctcctgga tatgatatta atgaatataa agattatttt    960

caatggaagt atggactaga tagaaatgca gatggaagtt atactgtgaa tagaaataaa   1020

tttaatgaaa tttataaaaa attatatagc tttacagaga ttgacttagc aaataaattt   1080

aaagtaaaat gtagaaatac ttattttatt aaatatggat ttgtaaaagt tccaaatttg   1140

ttagatgatg atatttatac tgtatcagag ggtttaata taggtaattt agcagtaaac   1200

aatcgcggac aaaatataaa tttaaatcct aaaattattg attccattcc agataaaggt   1260

ttagtggaaa agattattaa attttgtaag agcattattc ctagaaaagg tacgaagcag   1320

tcaccgtcac tatgcattag agtaaataat agggagttat tttttgtagc ttcagaaagt   1380

agctataatg aaagtgatat taatacacct aaagaaattg acgatacaac aaatctaaat   1440

aataattata gaaataattt agatgaagtt attttagatt ataatagtga gacaatacct   1500

caaatatcaa atcgaacatt aaatacactt gtacaagaca atagttatgt gccaagatat   1560

gattctaatg gaacaagtga aatagaggaa tatgatgttg ttgactttaa tgtatttttc   1620

tatttacatg cacaaaaagt accagaaggt gaaaccaata taagtttaac ttcttcaatt   1680

gatacagcat tattagaaga atccaaagta tatacatttt tttcttcaga gtttatcgat   1740

actatcaata aacctgtaaa tgcagcacta tttatagatt ggataagcaa agtaataaga   1800

gattttacca ctgaagctac acaaaaaagt actgttgata agattgcaga catatcttta   1860

attgtaccct atgtaggtct tgctttgaat atagttattg aggcagaaaa aggaaatttt   1920

gaggaggcat ttgaattatt aggagcgggt attttattag aatttgtgcc agagcttaca   1980

attcctgtaa ttttagtgtt tacgataaaa tcctatatag attcatatga gaataaaaat   2040
```

```
aaagcaatta aagcaataaa taattcatta atcgaaagag aagcaaagtg gaaagaaata   2100

tatagttgga tagtatcaaa ttggcttact agaattaata cgcaatttaa taaaagaaaa   2160

gagcaaatgt atcaggcttt acaaaatcaa gtagatgcaa taaaaacagc aatagaatat   2220

aaatataata attatacttc agatgagaaa aatagacttg aatctaaata taatatcaat   2280

aatatagaag aagaattgaa taaaaaagtt tctttagcaa tgaaaaatat agaaagattt   2340

atgacagaaa gttctatatc ttatttaatg aaattaataa atgaagccga agttggtaaa   2400

ttaaaagaat atgataaaca tgttaagagc gatttattag actatattct ctaccataaa   2460

ttaatcttag gagagcagac aaaggaatta attgatttgg tgactagtac tttgaatagt   2520

agtattccat ttgaactttc ttcatatact aatgataaaa ttctaattat atattttaat   2580

agattatata aaaaaattaa agatagttct attttagata tgcgatatga aaataataaa   2640

tttatagata tctctggata tggttcaaat ataagcatta atggaaacgt atatatttat   2700

tcaacaaata gaaatcaatt tggaatatat agtggtaggc ttagtgaagt taatatagct   2760

caaaataatg atattatata caatagtaga tatcaaaatt ttagtattag tttctgggta   2820

accattccta aacactacag acctatgaat cgtaatcggg aatacactat aataaattgt   2880

atggggaata ataattcggg atggaaaata tcacttagaa ctattagaga ttgtgaaata   2940

atttggactt tacaagatac ttccggaaat aaggaaaaat taatttttag gtatgaagaa   3000

cttgctagta tatctgatta tataaataaa tggattttg taactattac taataataga   3060

ttaggcaatt ctagaattta catcaatgga aatttaatag ttgaaaaatc aatttcgaat   3120

ttaggtgata ttcatgttag tgataatata ttatttaaaa ttgttggttg tgatgatgaa   3180

acgtatgttg gtataagata ttttaaagtt tttaatacgg aattagataa aacagaaatt   3240

gagactttat atagtaatga gccagatcca agtatcttaa aagactattg gggaaattat   3300

ttgctatata ataaaaaata ttatttattc aatttactaa gaaaagataa gtatattact   3360

cggaattcag gcattttaaa tattaatcaa caaagaggtg ttactggagg catatctgtt   3420

tttttgaact ataaattata tgaaggagta gaagttatta taagaaaaaa tgctcctata   3480

gatatatcta atacagataa ttttgttaga aaaaacgatc tagcatacat taatgtagta   3540

gatcatggtg tagaatatcg gttatatgct gatatatcaa ttacaaaatc agagaaaata   3600

ataaaattaa taagaacatc taatccaaac gatagcttag gtcaaattat agttatggat   3660

tcaataggaa ataattgcac aatgaatttt caaaacaatg atgggagcaa tataggatta   3720

ctaggttttc attcagatga tttggttgct agtagttggt attataacca tatacgaaga   3780

aacactagca gtaatggatg cttttggagt tttatttcta aagagcatgg ttggaaagaa   3840

taa                                                                 3843
```

<210> SEQ ID NO 12
<211> LENGTH: 1280
<212> TYPE: PRT
<213> ORGANISM: Clostridium botulinum

<400> SEQUENCE: 12

```
Met Pro Val Val Ile Asn Ser Phe Asn Tyr Asn Asp Pro Val Asn Asp
1               5                   10                  15

Glu Thr Ile Leu Tyr Met Gln Lys Pro Tyr Glu Glu Arg Ser Arg Lys
            20                  25                  30

Tyr Tyr Lys Ala Phe Glu Ile Met Pro Asn Val Trp Ile Met Pro Glu
        35                  40                  45
```

-continued

```
Arg Asp Thr Ile Gly Thr Lys Pro Asp Glu Phe Gln Val Pro Asp Ser
    50                  55                  60

Leu Lys Asn Gly Ser Ser Ala Tyr Tyr Asp Pro Asn Tyr Leu Thr Thr
65                  70                  75                  80

Asp Ala Glu Lys Asp Arg Tyr Leu Lys Thr Met Ile Lys Leu Phe Asn
                85                  90                  95

Arg Ile Asn Ser Asn Pro Thr Gly Lys Val Leu Leu Glu Glu Val Ser
            100                 105                 110

Asn Ala Arg Pro Tyr Leu Gly Asp Asp Asp Thr Leu Ile Asn Glu Phe
        115                 120                 125

Leu Pro Val Asn Val Thr Thr Ser Val Asn Ile Lys Phe Ser Thr Asp
    130                 135                 140

Val Glu Ser Ser Ile Ile Ser Asn Leu Leu Val Leu Gly Ala Gly Pro
145                 150                 155                 160

Asp Ile Phe Lys Ala Tyr Cys Thr Pro Leu Val Arg Phe Asn Lys Ser
                165                 170                 175

Asp Lys Leu Ile Glu Pro Ser Asn His Gly Phe Gly Ser Ile Asn Ile
            180                 185                 190

Leu Thr Phe Ser Pro Glu Tyr Glu His Ile Phe Asn Asp Ile Ser Gly
        195                 200                 205

Gly Asn His Asn Ser Thr Glu Ser Phe Ile Ala Asp Pro Ala Ile Ser
    210                 215                 220

Leu Ala His Glu Leu Ile His Ala Leu His Gly Leu Tyr Gly Ala Lys
225                 230                 235                 240

Ala Val Thr His Lys Glu Ser Leu Val Ala Glu Arg Gly Pro Leu Met
                245                 250                 255

Ile Ala Glu Lys Pro Ile Arg Leu Glu Glu Phe Leu Thr Phe Gly Gly
            260                 265                 270

Glu Asp Leu Asn Ile Ile Pro Ser Ala Met Lys Glu Lys Ile Tyr Asn
        275                 280                 285

Asp Leu Leu Ala Asn Tyr Glu Lys Ile Ala Thr Arg Leu Arg Glu Val
    290                 295                 300

Asn Thr Ala Pro Pro Gly Tyr Asp Ile Asn Glu Tyr Lys Asp Tyr Phe
305                 310                 315                 320

Gln Trp Lys Tyr Gly Leu Asp Arg Asn Ala Asp Gly Ser Tyr Thr Val
                325                 330                 335

Asn Arg Asn Lys Phe Asn Glu Ile Tyr Lys Lys Leu Tyr Ser Phe Thr
            340                 345                 350

Glu Ile Asp Leu Ala Asn Lys Phe Lys Val Lys Cys Arg Asn Thr Tyr
        355                 360                 365

Phe Ile Lys Tyr Gly Phe Val Lys Val Pro Asn Leu Leu Asp Asp Asp
    370                 375                 380

Ile Tyr Thr Val Ser Glu Gly Phe Asn Ile Gly Asn Leu Ala Val Asn
385                 390                 395                 400

Asn Arg Gly Gln Asn Ile Asn Leu Asn Pro Lys Ile Ile Asp Ser Ile
                405                 410                 415

Pro Asp Lys Gly Leu Val Glu Lys Ile Ile Lys Phe Cys Lys Ser Ile
            420                 425                 430

Ile Pro Arg Lys Gly Thr Lys Gln Ser Pro Ser Leu Cys Ile Arg Val
        435                 440                 445

Asn Asn Arg Glu Leu Phe Phe Val Ala Ser Glu Ser Ser Tyr Asn Glu
    450                 455                 460

Ser Asp Ile Asn Thr Pro Lys Glu Ile Asp Asp Thr Thr Asn Leu Asn
```

```
465                 470                 475                 480

Asn Asn Tyr Arg Asn Asn Leu Asp Glu Val Ile Leu Asp Tyr Asn Ser
                485                 490                 495

Glu Thr Ile Pro Gln Ile Ser Asn Arg Thr Leu Asn Thr Leu Val Gln
            500                 505                 510

Asp Asn Ser Tyr Val Pro Arg Tyr Asp Ser Asn Gly Thr Ser Glu Ile
        515                 520                 525

Glu Glu Tyr Asp Val Val Asp Phe Asn Val Phe Phe Tyr Leu His Ala
    530                 535                 540

Gln Lys Val Pro Glu Gly Glu Thr Asn Ile Ser Leu Thr Ser Ser Ile
545                 550                 555                 560

Asp Thr Ala Leu Leu Glu Glu Ser Lys Val Tyr Thr Phe Phe Ser Ser
                565                 570                 575

Glu Phe Ile Asp Thr Ile Asn Lys Pro Val Asn Ala Ala Leu Phe Ile
            580                 585                 590

Asp Trp Ile Ser Lys Val Ile Arg Asp Phe Thr Thr Glu Ala Thr Gln
        595                 600                 605

Lys Ser Thr Val Asp Lys Ile Ala Asp Ile Ser Leu Ile Val Pro Tyr
    610                 615                 620

Val Gly Leu Ala Leu Asn Ile Val Ile Glu Ala Glu Lys Gly Asn Phe
625                 630                 635                 640

Glu Glu Ala Phe Glu Leu Leu Gly Ala Gly Ile Leu Leu Glu Phe Val
                645                 650                 655

Pro Glu Leu Thr Ile Pro Val Ile Leu Val Phe Thr Ile Lys Ser Tyr
            660                 665                 670

Ile Asp Ser Tyr Glu Asn Lys Asn Lys Ala Ile Lys Ala Ile Asn Asn
        675                 680                 685

Ser Leu Ile Glu Arg Glu Ala Lys Trp Lys Glu Ile Tyr Ser Trp Ile
    690                 695                 700

Val Ser Asn Trp Leu Thr Arg Ile Asn Thr Gln Phe Asn Lys Arg Lys
705                 710                 715                 720

Glu Gln Met Tyr Gln Ala Leu Gln Asn Gln Val Asp Ala Ile Lys Thr
                725                 730                 735

Ala Ile Glu Tyr Lys Tyr Asn Asn Tyr Thr Ser Asp Glu Lys Asn Arg
            740                 745                 750

Leu Glu Ser Lys Tyr Asn Ile Asn Asn Ile Glu Glu Glu Leu Asn Lys
        755                 760                 765

Lys Val Ser Leu Ala Met Lys Asn Ile Glu Arg Phe Met Thr Glu Ser
    770                 775                 780

Ser Ile Ser Tyr Leu Met Lys Leu Ile Asn Glu Ala Glu Val Gly Lys
785                 790                 795                 800

Leu Lys Glu Tyr Asp Lys His Val Lys Ser Asp Leu Leu Asp Tyr Ile
                805                 810                 815

Leu Tyr His Lys Leu Ile Leu Gly Glu Gln Thr Lys Glu Leu Ile Asp
            820                 825                 830

Leu Val Thr Ser Thr Leu Asn Ser Ser Ile Pro Phe Glu Leu Ser Ser
        835                 840                 845

Tyr Thr Asn Asp Lys Ile Leu Ile Ile Tyr Phe Asn Arg Leu Tyr Lys
    850                 855                 860

Lys Ile Lys Asp Ser Ser Ile Leu Asp Met Arg Tyr Glu Asn Asn Lys
865                 870                 875                 880

Phe Ile Asp Ile Ser Gly Tyr Gly Ser Asn Ile Ser Ile Asn Gly Asn
                885                 890                 895
```

```
Val Tyr Ile Tyr Ser Thr Asn Arg Asn Gln Phe Gly Ile Tyr Ser Gly
            900                 905                 910

Arg Leu Ser Glu Val Asn Ile Ala Gln Asn Asn Asp Ile Ile Tyr Asn
        915                 920                 925

Ser Arg Tyr Gln Asn Phe Ser Ile Ser Phe Trp Val Thr Ile Pro Lys
    930                 935                 940

His Tyr Arg Pro Met Asn Arg Asn Arg Glu Tyr Thr Ile Ile Asn Cys
945                 950                 955                 960

Met Gly Asn Asn Asn Ser Gly Trp Lys Ile Ser Leu Arg Thr Ile Arg
                965                 970                 975

Asp Cys Glu Ile Ile Trp Thr Leu Gln Asp Thr Ser Gly Asn Lys Glu
            980                 985                 990

Lys Leu Ile Phe Arg Tyr Glu Glu  Leu Ala Ser Ile Ser  Asp Tyr Ile
        995                 1000                1005

Asn Lys  Trp Ile Phe Val Thr  Ile Thr Asn Asn Arg  Leu Gly Asn
    1010                1015                1020

Ser Arg  Ile Tyr Ile Asn Gly  Asn Leu Ile Val Glu  Lys Ser Ile
    1025                1030                1035

Ser Asn  Leu Gly Asp Ile His  Val Ser Asp Asn Ile  Leu Phe Lys
    1040                1045                1050

Ile Val  Gly Cys Asp Asp Glu  Thr Tyr Val Gly Ile  Arg Tyr Phe
    1055                1060                1065

Lys Val  Phe Asn Thr Glu Leu  Asp Lys Thr Glu Ile  Glu Thr Leu
    1070                1075                1080

Tyr Ser  Asn Glu Pro Asp Pro  Ser Ile Leu Lys Asp  Tyr Trp Gly
    1085                1090                1095

Asn Tyr  Leu Leu Tyr Asn Lys  Lys Tyr Tyr Leu Phe  Asn Leu Leu
    1100                1105                1110

Arg Lys  Asp Lys Tyr Ile Thr  Arg Asn Ser Gly Ile  Leu Asn Ile
    1115                1120                1125

Asn Gln  Gln Arg Gly Val Thr  Gly Gly Ile Ser Val  Phe Leu Asn
    1130                1135                1140

Tyr Lys  Leu Tyr Glu Gly Val  Glu Val Ile Ile Arg  Lys Asn Ala
    1145                1150                1155

Pro Ile  Asp Ile Ser Asn Thr  Asp Asn Phe Val Arg  Lys Asn Asp
    1160                1165                1170

Leu Ala  Tyr Ile Asn Val Val  Asp His Gly Val Glu  Tyr Arg Leu
    1175                1180                1185

Tyr Ala  Asp Ile Ser Ile Thr  Lys Ser Glu Lys Ile  Ile Lys Leu
    1190                1195                1200

Ile Arg  Thr Ser Asn Pro Asn  Asp Ser Leu Gly Gln  Ile Ile Val
    1205                1210                1215

Met Asp  Ser Ile Gly Asn Asn  Cys Thr Met Asn Phe  Gln Asn Asn
    1220                1225                1230

Asp Gly  Ser Asn Ile Gly Leu  Leu Gly Phe His Ser  Asp Asp Leu
    1235                1240                1245

Val Ala  Ser Ser Trp Tyr Tyr  Asn His Ile Arg Arg  Asn Thr Ser
    1250                1255                1260

Ser Asn  Gly Cys Phe Trp Ser  Phe Ile Ser Lys Glu  His Gly Trp
    1265                1270                1275

Lys Glu
    1280
```

<210> SEQ ID NO 13
<211> LENGTH: 3894
<212> TYPE: DNA
<213> ORGANISM: Clostridium botulinum
<220> FEATURE:
<221> NAME/KEY: misc_feature
<222> LOCATION: (20)..(20)
<223> OTHER INFORMATION: n is a, c, g, or t

<400> SEQUENCE: 13
atgccagtta atataaaaan ctttaattat aatgacccta ttaataatga tgacattatt 60
atgatggaac cattcaatga cccagggcca ggaacatatt ataaagcttt taggattata 120
gatcgtattt ggatagtacc agaaaggttt acttatggat ttcaacctga ccaatttaat 180
gccagtacag gagtttttag taaagatgtc tacgaatatt acgatccaac ttatttaaaa 240
accgatgctg aaaaagataa atttttaaaa acaatgatta aattatttaa tagaattaat 300
tcaaaaccat caggacagag attactggat atgatagtag atgctatacc ttatcttgga 360
aatgcatcta caccgcccga caaatttgca gcaaatgttg caaatgtatc tattaataaa 420
aaaattatcc aacctggagc tgaagatcaa ataaaaggtt taatgacaaa tttaataata 480
tttggaccag gaccagttct aagtgataat tttactgata gtatgattat gaatggccat 540
tccccaatat cagaaggatt tggtgcaaga atgatgataa gattttgtcc tagttgttta 600
aatgtattta ataatgttca ggaaaataaa gatacatcta tatttagtag acgcgcgtat 660
tttgcagatc cagctctaac gttaatgcat gaacttatac atgtgttaca tggattatat 720
ggaattaaga taagtaattt accaattact ccaaatacaa aagaattttt catgcaacat 780
agcgatcctg tacaagcaga agaactatat acattcggag gacatgatcc tagtgttata 840
agtccttcta cggatatgaa tatttataat aaagcgttac aaaattttca agatatagct 900
aataggctta atattgtttc aagtgcccaa gggagtggaa ttgatatttc cttatataaa 960
caaatatata aaaataaata tgattttgtt gaagatccta atggaaaata tagtgtagat 1020
aaggataagt ttgataaatt atataaggcc ttaatgtttg gctttactga aactaatcta 1080
gctggtgaat atggaataaa aactaggtat tcttatttta gtgaatattt gccaccgata 1140
aaaactgaaa aattgttaga caatacaatt tatactcaaa atgaaggctt taacatagct 1200
agtaaaaatc tcaaaacgga atttaatggt cagaataagg cggtaaataa agaggcttat 1260
gaagaaatca gcctagaaca tctcgttata tatagaatag caatgtgcaa gcctgtaatg 1320
tacaaaaata ccggtaaatc tgaacagtgt attattgtta ataatgagga tttatttttc 1380
atagctaata aagatagttt ttcaaaagat ttagctaaag cagaaactat agcatataat 1440
acacaaaata atactataga aaataatttt tctatagatc agttgatttt agataatgat 1500
ttaagcagtg gcatagactt accaaatgaa aacacagaac catttacaaa ttttgacgac 1560
atagatatcc ctgtgtatat taaacaatct gctttaaaaa aaatttttgt ggatggagat 1620 agccttttttg aatatttaca tgctcaaaca tttccttcta atatagaaaa tctacaacta 1680
acgaattcat taaatgatgc tttaagaaat aataataaag tctatacttt tttttctaca 1740
aaccttgttg aaaaagctaa tacagttgta ggtgcttcac tttttgtaaa ctgggtaaaa 1800
ggagtaatag atgattttac atctgaatcc acacaaaaaa gtactataga taaagtttca 1860
gatgtatcca taattattcc ctatatagga cctgctttga atgtaggaaa tgaaacagct 1920
aaagaaaatt ttaaaaatgc ttttgaaata ggtggagccg ctatcttaat ggagtttatt 1980
ccagaactta ttgtacctat agttggattt tttacattag aatcatatgt aggaaataaa 2040

```
gggcatatta ttatgacgat atccaatgct ttaaagaaaa gggatcaaaa atggacagat   2100

atgtatggtt tgatagtatc gcagtggctc tcaacggtta atactcaatt ttatacaata   2160

aaagaaagaa tgtacaatgc tttaaataat caatcacaag caatagaaaa aataatagaa   2220

gatcaatata atagatatag tgaagaagat aaaatgaata ttaacattga ttttaatgat   2280

atagatttta aacttaatca aagtataaat ttagcaataa acaatataga tgattttata   2340

aaccaatgtt ctatatcata tctaatgaat agaatgattc cattagctgt aaaaaagtta   2400

aaagactttg atgataatct taagagagat ttattggagt atatagatac aaatgaacta   2460

tatttacttg atgaagtaaa tattctaaaa tcaaaagtaa atagacacct aaaagacagt   2520

ataccatttg atctttcact atataccaag gacacaattt taatacaagt ttttaataat   2580

tatattagta atattagtag taatgctatt ttaagtttaa gttatagagg tgggcgttta   2640

atagattcat ctggatatgg tgcaactatg aatgtaggtt cagatgttat ctttaatgat   2700

ataggaaatg gtcaatttaa attaaataat tctgaaaata gtaatattac ggcacatcaa   2760

agtaaattcg ttgtatatga tagtatgttt gataatttta gcattaactt ttgggtaagg   2820

actcctaaat ataataataa tgatatacaa acttatcttc aaaatgagta tacaataatt   2880

agttgtataa aaaatgactc aggatggaaa gtatctatta agggaaatag aataatatgg   2940

acattaatag atgttaatgc aaaatctaaa tcaatatttt tcgaatatag tataaaagat   3000

aatatatcag attatataaa taaatggttt tccataacta ttactaatga tagattaggt   3060

aacgcaaata tttatataaa tggaagtttg aaaaaaagtg aaaaaatttt aaacttagat   3120

agaattaatt ctagtaatga tatagacttc aaattaatta attgtacaga tactactaaa   3180

tttgtttgga ttaaggattt taatattttt ggtagagaat taaatgctac agaagtatct   3240

tcactatatt ggattcaatc atctacaaat actttaaaag atttttgggg gaatccttta   3300

agatacgata cacaatacta tctgtttaat caaggtatgc aaaatatcta tataaagtat   3360

tttagtaaag cttctatggg ggaaactgca ccacgtacaa actttaataa tgcagcaata   3420

aattatcaaa atttatatct tggtttacga tttattataa aaaaagcatc aaattctcgg   3480

aatataaata atgataatat agtcagagaa ggagattata tatatcttaa tattgataat   3540

atttctgatg aatcttacag agtatatgtt ttggtgaatt ctaaagaaat tcaaactcaa   3600

ttatttttag cacccataaa tgatgatcct acgttctatg atgtactaca aataaaaaaa   3660

tattatgaaa aaacaacata taattgtcag atactttgcg aaaaagatac taaaacattt   3720

gggctgtttg gaattggtaa atttgttaaa gattatggat atgtttggga tacctatgat   3780

aattattttt gcataagtca gtggtatctc agaagaatat ctgaaaatat aaataaatta   3840

aggttgggat gtaattggca attcattccc gtggatgaag gatggacaga ataa          3894
```

<210> SEQ ID NO 14
<211> LENGTH: 1297
<212> TYPE: PRT
<213> ORGANISM: Clostridium botulinum
<220> FEATURE:
<221> NAME/KEY: misc_feature
<222> LOCATION: (7)..(7)
<223> OTHER INFORMATION: Xaa can be any naturally occurring amino acid

<400> SEQUENCE: 14

```
Met Pro Val Asn Ile Lys Xaa Phe Asn Tyr Asn Asp Pro Ile Asn Asn
1               5                   10                  15

Asp Asp Ile Ile Met Met Glu Pro Phe Asn Asp Pro Gly Pro Gly Thr
```

```
            20                  25                  30

Tyr Tyr Lys Ala Phe Arg Ile Ile Asp Arg Ile Trp Ile Val Pro Glu
        35                  40                  45

Arg Phe Thr Tyr Gly Phe Gln Pro Asp Gln Phe Asn Ala Ser Thr Gly
    50                  55                  60

Val Phe Ser Lys Asp Val Tyr Glu Tyr Tyr Asp Pro Thr Tyr Leu Lys
65                  70                  75                  80

Thr Asp Ala Glu Lys Asp Lys Phe Leu Lys Thr Met Ile Lys Leu Phe
                85                  90                  95

Asn Arg Ile Asn Ser Lys Pro Ser Gly Gln Arg Leu Leu Asp Met Ile
            100                 105                 110

Val Asp Ala Ile Pro Tyr Leu Gly Asn Ala Ser Thr Pro Pro Asp Lys
        115                 120                 125

Phe Ala Ala Asn Val Ala Asn Val Ser Ile Asn Lys Lys Ile Ile Gln
    130                 135                 140

Pro Gly Ala Glu Asp Gln Ile Lys Gly Leu Met Thr Asn Leu Ile Ile
145                 150                 155                 160

Phe Gly Pro Gly Pro Val Leu Ser Asp Asn Phe Thr Asp Ser Met Ile
                165                 170                 175

Met Asn Gly His Ser Pro Ile Ser Glu Gly Phe Gly Ala Arg Met Met
            180                 185                 190

Ile Arg Phe Cys Pro Ser Cys Leu Asn Val Phe Asn Asn Val Gln Glu
        195                 200                 205

Asn Lys Asp Thr Ser Ile Phe Ser Arg Arg Ala Tyr Phe Ala Asp Pro
    210                 215                 220

Ala Leu Thr Leu Met His Glu Leu Ile His Val Leu His Gly Leu Tyr
225                 230                 235                 240

Gly Ile Lys Ile Ser Asn Leu Pro Ile Thr Pro Asn Thr Lys Glu Phe
                245                 250                 255

Phe Met Gln His Ser Asp Pro Val Gln Ala Glu Glu Leu Tyr Thr Phe
            260                 265                 270

Gly Gly His Asp Pro Ser Val Ile Ser Pro Ser Thr Asp Met Asn Ile
        275                 280                 285

Tyr Asn Lys Ala Leu Gln Asn Phe Gln Asp Ile Ala Asn Arg Leu Asn
    290                 295                 300

Ile Val Ser Ser Ala Gln Gly Ser Gly Ile Asp Ile Ser Leu Tyr Lys
305                 310                 315                 320

Gln Ile Tyr Lys Asn Lys Tyr Asp Phe Val Glu Asp Pro Asn Gly Lys
                325                 330                 335

Tyr Ser Val Asp Lys Asp Lys Phe Asp Lys Leu Tyr Lys Ala Leu Met
            340                 345                 350

Phe Gly Phe Thr Glu Thr Asn Leu Ala Gly Glu Tyr Gly Ile Lys Thr
        355                 360                 365

Arg Tyr Ser Tyr Phe Ser Glu Tyr Leu Pro Pro Ile Lys Thr Glu Lys
    370                 375                 380

Leu Leu Asp Asn Thr Ile Tyr Thr Gln Asn Glu Gly Phe Asn Ile Ala
385                 390                 395                 400

Ser Lys Asn Leu Lys Thr Glu Phe Asn Gly Gln Asn Lys Ala Val Asn
                405                 410                 415

Lys Glu Ala Tyr Glu Glu Ile Ser Leu Glu His Leu Val Ile Tyr Arg
            420                 425                 430

Ile Ala Met Cys Lys Pro Val Met Tyr Lys Asn Thr Gly Lys Ser Glu
        435                 440                 445
```

```
Gln Cys Ile Ile Val Asn Asn Glu Asp Leu Phe Phe Ile Ala Asn Lys
    450                 455                 460

Asp Ser Phe Ser Lys Asp Leu Ala Lys Ala Glu Thr Ile Ala Tyr Asn
465                 470                 475                 480

Thr Gln Asn Asn Thr Ile Glu Asn Asn Phe Ser Ile Asp Gln Leu Ile
                485                 490                 495

Leu Asp Asn Asp Leu Ser Ser Gly Ile Asp Leu Pro Asn Glu Asn Thr
            500                 505                 510

Glu Pro Phe Thr Asn Phe Asp Asp Ile Asp Ile Pro Val Tyr Ile Lys
        515                 520                 525

Gln Ser Ala Leu Lys Lys Ile Phe Val Asp Gly Asp Ser Leu Phe Glu
    530                 535                 540

Tyr Leu His Ala Gln Thr Phe Pro Ser Asn Ile Glu Asn Leu Gln Leu
545                 550                 555                 560

Thr Asn Ser Leu Asn Asp Ala Leu Arg Asn Asn Asn Lys Val Tyr Thr
                565                 570                 575

Phe Phe Ser Thr Asn Leu Val Glu Lys Ala Asn Thr Val Val Gly Ala
            580                 585                 590

Ser Leu Phe Val Asn Trp Val Lys Gly Val Ile Asp Asp Phe Thr Ser
        595                 600                 605

Glu Ser Thr Gln Lys Ser Thr Ile Asp Lys Val Ser Asp Val Ser Ile
    610                 615                 620

Ile Ile Pro Tyr Ile Gly Pro Ala Leu Asn Val Gly Asn Glu Thr Ala
625                 630                 635                 640

Lys Glu Asn Phe Lys Asn Ala Phe Glu Ile Gly Gly Ala Ala Ile Leu
                645                 650                 655

Met Glu Phe Ile Pro Glu Leu Ile Val Pro Ile Val Gly Phe Phe Thr
            660                 665                 670

Leu Glu Ser Tyr Val Gly Asn Lys Gly His Ile Ile Met Thr Ile Ser
        675                 680                 685

Asn Ala Leu Lys Lys Arg Asp Gln Lys Trp Thr Asp Met Tyr Gly Leu
    690                 695                 700

Ile Val Ser Gln Trp Leu Ser Thr Val Asn Thr Gln Phe Tyr Thr Ile
705                 710                 715                 720

Lys Glu Arg Met Tyr Asn Ala Leu Asn Asn Gln Ser Gln Ala Ile Glu
                725                 730                 735

Lys Ile Ile Glu Asp Gln Tyr Asn Arg Tyr Ser Glu Glu Asp Lys Met
            740                 745                 750

Asn Ile Asn Ile Asp Phe Asn Asp Ile Asp Phe Lys Leu Asn Gln Ser
        755                 760                 765

Ile Asn Leu Ala Ile Asn Asn Ile Asp Asp Phe Ile Asn Gln Cys Ser
    770                 775                 780

Ile Ser Tyr Leu Met Asn Arg Met Ile Pro Leu Ala Val Lys Lys Leu
785                 790                 795                 800

Lys Asp Phe Asp Asp Asn Leu Lys Arg Asp Leu Leu Glu Tyr Ile Asp
                805                 810                 815

Thr Asn Glu Leu Tyr Leu Leu Asp Glu Val Asn Ile Leu Lys Ser Lys
            820                 825                 830

Val Asn Arg His Leu Lys Asp Ser Ile Pro Phe Asp Leu Ser Leu Tyr
        835                 840                 845

Thr Lys Asp Thr Ile Leu Ile Gln Val Phe Asn Asn Tyr Ile Ser Asn
    850                 855                 860
```

```
Ile Ser Ser Asn Ala Ile Leu Ser Leu Ser Tyr Arg Gly Gly Arg Leu
865                 870                 875                 880

Ile Asp Ser Ser Gly Tyr Gly Ala Thr Met Asn Val Gly Ser Asp Val
                885                 890                 895

Ile Phe Asn Asp Ile Gly Asn Gly Gln Phe Lys Leu Asn Asn Ser Glu
            900                 905                 910

Asn Ser Asn Ile Thr Ala His Gln Ser Lys Phe Val Val Tyr Asp Ser
        915                 920                 925

Met Phe Asp Asn Phe Ser Ile Asn Phe Trp Val Arg Thr Pro Lys Tyr
    930                 935                 940

Asn Asn Asn Asp Ile Gln Thr Tyr Leu Gln Asn Glu Tyr Thr Ile Ile
945                 950                 955                 960

Ser Cys Ile Lys Asn Asp Ser Gly Trp Lys Val Ser Ile Lys Gly Asn
                965                 970                 975

Arg Ile Ile Trp Thr Leu Ile Asp Val Asn Ala Lys Ser Lys Ser Ile
            980                 985                 990

Phe Phe Glu Tyr Ser Ile Lys Asp  Asn Ile Ser Asp Tyr  Ile Asn Lys
        995                 1000                 1005

Trp Phe  Ser Ile Thr Ile Thr  Asn Asp Arg Leu Gly  Asn Ala Asn
    1010                 1015                 1020

Ile Tyr  Ile Asn Gly Ser Leu  Lys Lys Ser Glu Lys  Ile Leu Asn
    1025                 1030                 1035

Leu Asp  Arg Ile Asn Ser Ser  Asn Asp Ile Asp Phe  Lys Leu Ile
    1040                 1045                 1050

Asn Cys  Thr Asp Thr Thr Lys  Phe Val Trp Ile Lys  Asp Phe Asn
    1055                 1060                 1065

Ile Phe  Gly Arg Glu Leu Asn  Ala Thr Glu Val Ser  Ser Leu Tyr
    1070                 1075                 1080

Trp Ile  Gln Ser Ser Thr Asn  Thr Leu Lys Asp Phe  Trp Gly Asn
    1085                 1090                 1095

Pro Leu  Arg Tyr Asp Thr Gln  Tyr Tyr Leu Phe Asn  Gln Gly Met
    1100                 1105                 1110

Gln Asn  Ile Tyr Ile Lys Tyr  Phe Ser Lys Ala Ser  Met Gly Glu
    1115                 1120                 1125

Thr Ala  Pro Arg Thr Asn Phe  Asn Asn Ala Ala Ile  Asn Tyr Gln
    1130                 1135                 1140

Asn Leu  Tyr Leu Gly Leu Arg  Phe Ile Ile Lys Lys  Ala Ser Asn
    1145                 1150                 1155

Ser Arg  Asn Ile Asn Asn Asp  Asn Ile Val Arg Glu  Gly Asp Tyr
    1160                 1165                 1170

Ile Tyr  Leu Asn Ile Asp Asn  Ile Ser Asp Glu Ser  Tyr Arg Val
    1175                 1180                 1185

Tyr Val  Leu Val Asn Ser Lys  Glu Ile Gln Thr Gln  Leu Phe Leu
    1190                 1195                 1200

Ala Pro  Ile Asn Asp Asp Pro  Thr Phe Tyr Asp Val  Leu Gln Ile
    1205                 1210                 1215

Lys Lys  Tyr Tyr Glu Lys Thr  Thr Tyr Asn Cys Gln  Ile Leu Cys
    1220                 1225                 1230

Glu Lys  Asp Thr Lys Thr Phe  Gly Leu Phe Gly Ile  Gly Lys Phe
    1235                 1240                 1245

Val Lys  Asp Tyr Gly Tyr Val  Trp Asp Thr Tyr Asp  Asn Tyr Phe
    1250                 1255                 1260

Cys Ile  Ser Gln Trp Tyr Leu  Arg Arg Ile Ser Glu  Asn Ile Asn
```

```
    1265                1270                1275

Lys Leu  Arg Leu Gly Cys Asn  Trp Gln Phe Ile Pro  Val Asp Glu
    1280                1285                1290

Gly Trp  Thr Glu
    1295


<210> SEQ ID NO 15
<211> LENGTH: 4400
<212> TYPE: DNA
<213> ORGANISM: Clostridium tetani

<400> SEQUENCE: 15

tagcattaaa aaaattagaa cctatagtaa ataaattaat taatatatag tttttataat      60
ttaattatga ataatattct taagataaaa agtaaatttt taaaaattta aattttcagt     120
ttacaaaaaa taacctgatt atgttatatg taattgtaaa aaacatataa aaaatcagaa     180
aaatttagga ggtatattat taatggatta aataataatt ttttaattta cttttgatta     240
ataaatatta aatgtttatt ttaattagga gatgatacgt atgccaataa ccataaataa     300
ttttagatat agtgatcctg ttaataatga tacaattatt atgatggagc caccatactg     360
taagggtcta gatatctatt ataaggcttt caaaataaca gatcgtattt ggatagtgcc     420
ggaaaggtat gaatttggga caaaacctga agattttaac ccaccatctt cattaataga     480
aggtgcatct gagtattacg atccaaatta tttaaggact gattctgata aagatagatt     540
tttacaaacc atggtaaaac tgtttaacag aattaaaaac aatgtagcag gtgaagcctt     600
attagataag ataataaatg ccatacctta ccttggaaat tcatattcct tactagacaa     660
gtttgataca aactctaatt cagtatcttt taatttatta gaacaagacc ccagtggagc     720
aactacaaaa tcagcaatgc tgacaaattt aataatattt ggacctgggc ctgttttaaa     780
taaaaatgag gttagaggta ttgtattgag ggtagataat aaaaattact tcccatgtag     840
agatggtttt ggctcaataa tgcaaatggc attttgccca gaatatgtac ctacctttga     900
taatgtaata gaaaatatta cgtcactcac tattggcaaa agcaaatatt ttcaagatcc     960
agcattacta ttaatgcacg aacttataca tgtactacat ggtttatacg gaatgcaggt    1020
atcaagccat gaaattattc catccaaaca agaaatttat atgcagcata catatccaat    1080
aagtgctgaa gaactattca cttttggcgg acaggatgct aatcttataa gtattgatat    1140
aaaaaacgat ttatatgaaa aaactttaaa tgattataaa gctatagcta acaaacttag    1200
tcaagtcact agctgcaatg atcccaacat tgatattgat agctacaaac aaatatatca    1260
acaaaaatat caattcgata aagatagcaa tggacaatat attgtaaatg aggataaatt    1320
tcagatacta tataatagca taatgtatgg ttttacagag attgaattgg gaaaaaaatt    1380
taatataaaa actagacttt cttattttag tatgaatcat gaccctgtaa aaattccaaa    1440
tttattagat gatacaattt acaatgatac agaaggattt aatatagaaa gcaaagatct    1500
gaaatctgaa tataaaggac aaaatatgag ggtaaataca aatgctttta gaaatgttga    1560
tggatcaggc ctagtttcaa aacttattgg cttatgtaaa aaaattatac caccaacaaa    1620
tataagagaa aatttatata atagaactgc atcattaaca gatttaggag gagaattatg    1680
tataaaaatt aaaaatgaag atttaacttt tatagctgaa aaaaatagct tttcagaaga    1740
accatttcaa gatgaaatag ttagttataa tacaaaaaat aaaccattaa attttaatta    1800
ttcgctagat aaaattattg tagattataa tctacaaagt aaaattacat tacctaatga    1860
taggacaacc ccagttacaa aaggaattcc atatgctcca gaatataaaa gtaatgctgc    1920
```

```
aagtacaata gaaatacata atattgatga caatacaata tatcaatatt tgtatgctca   1980
aaaatctcct acaactctac aaagaataac tatgactaat tctgttgatg acgcattaat   2040
aaattccacc aaaatatatt catattttcc atctgtaatc agtaaagtta accaaggtgc   2100
acaaggaatt ttattcttac agtgggtgag agatataatt gatgatttta ccaatgaatc   2160
ttcacaaaaa actactattg ataaaatttc agatgtatcc actattgttc cttatatagg   2220
acccgcatta aacattgtaa aacaaggcta tgagggaaac tttataggcg ctttagaaac   2280
taccggagtg gttttattat tagaatatat tccagaaatt actttaccag taattgcagc   2340
tttatctata gcagaaagta gcacacaaaa agaaaagata ataaaaacaa tagataactt   2400
tttagaaaaa agatatgaaa aatggattga agtatataaa ctagtaaaag caaaatggtt   2460
aggcacagtt aatacgcaat tccaaaaaag aagttatcaa atgtatagat ctttagaata   2520
tcaagtagat gcaataaaaa aaataataga ctatgaatat aaaatatatt caggacctga   2580
taaggaacaa attgccgacg aaattaataa tctgaaaaac aaacttgaag aaaaggctaa   2640
taaagcaatg ataaacataa atatatttat gagggaaagt tctagatcat ttttagttaa   2700
tcaaatgatt aacgaagcta aaaagcagtt attagagttt gatactcaaa gcaaaaatat   2760
tttaatgcag tatataaaag caaattctaa atttataggt ataactgaac taaaaaaatt   2820
agaatcaaaa ataaacaaag ttttttcaac accaattcca ttttcttatt ctaaaaatct   2880
ggattgttgg gttgataatg aagaagatat agatgttata ttaaaaaaga gtacaatttt   2940
aaatttagat attaataatg atattatatc agatatatct gggtttaatt catctgtaat   3000
aacatatcca gatgctcaat tggtgcccgg aataaatggc aaagcaatac atttagtaaa   3060
caatgaatct tctgaagtta tagtgcataa agctatggat attgaatata atgatatgtt   3120
taataatttt accgttagct tttggttgag ggttcctaaa gtatctgcta gtcatttaga   3180
acaatatggc acaaatgagt attcaataat tagctctatg aaaaaacata gtctatcaat   3240
aggatctggt tggagtgtat cacttaaagg taataactta atatggactt taaaagattc   3300
cgcgggagaa gttagacaaa taactttttag ggatttacct gataaattta atgcttattt   3360
agcaaataaa tgggttttta taactattac taatgataga ttatcttctg ctaatttgta   3420
tataaatgga gtacttatgg gaagtgcaga aattactggt ttaggagcta ttagagagga   3480
taataatata acattaaaac tagatagatg taataataat aatcaatacg tttctattga   3540
taaatttagg atattttgca aagcattaaa tccaaaagag attgaaaaat tatacacaag   3600
ttatttatct ataacctttt taagagactt ctggggaaac cctttacgat atgatacaga   3660
atattattta ataccagtag cttctagttc taaagatgtt caattgaaaa atataacaga   3720
ttatatgtat ttgacaaatg cgccatcgta tactaacgga aaattgaata tatattatag   3780
aaggttatat aatggactaa aatttattat aaaaagatat acacctaata atgaaataga   3840
ttcttttgtt aaatcaggtg attttattaa attatatgta tcatataaca ataatgagca   3900
cattgtaggt tatccgaaag atggaaatgc ctttaataat cttgatagaa ttctaagagt   3960
aggttataat gccccaggta tccctcttta taaaaaaatg gaagcagtaa aattgcgtga   4020
tttaaaaacc tattctgtac aacttaaatt atatgatgat aaaaatgcat ctttaggact   4080
agtaggtacc cataatggtc aaataggcaa cgatccaaat agggatatat taattgcaag   4140
caactggtac tttaatcatt taaaagataa aattttagga tgtgattggt actttgtacc   4200
tacagatgaa ggatggacaa atgattaaac agattgatat gttcatgatt actctatata   4260
```

```
aaaaattaaa taatataaca atctagctat attatttttg attattttct taatatatac   4320

taataaaata atcaaaatag agcctatctt aaattactga agggctgtgt caaaataaga   4380

ttttgacaca gcctctactt                                               4400


<210> SEQ ID NO 16
<211> LENGTH: 1315
<212> TYPE: PRT
<213> ORGANISM: Clostridium tetani

<400> SEQUENCE: 16

Met Pro Ile Thr Ile Asn Asn Phe Arg Tyr Ser Asp Pro Val Asn Asn
1               5                   10                  15

Asp Thr Ile Ile Met Met Glu Pro Pro Tyr Cys Lys Gly Leu Asp Ile
            20                  25                  30

Tyr Tyr Lys Ala Phe Lys Ile Thr Asp Arg Ile Trp Ile Val Pro Glu
        35                  40                  45

Arg Tyr Glu Phe Gly Thr Lys Pro Glu Asp Phe Asn Pro Pro Ser Ser
    50                  55                  60

Leu Ile Glu Gly Ala Ser Glu Tyr Tyr Asp Pro Asn Tyr Leu Arg Thr
65                  70                  75                  80

Asp Ser Asp Lys Asp Arg Phe Leu Gln Thr Met Val Lys Leu Phe Asn
                85                  90                  95

Arg Ile Lys Asn Asn Val Ala Gly Glu Ala Leu Leu Asp Lys Ile Ile
            100                 105                 110

Asn Ala Ile Pro Tyr Leu Gly Asn Ser Tyr Ser Leu Leu Asp Lys Phe
        115                 120                 125

Asp Thr Asn Ser Asn Ser Val Ser Phe Asn Leu Leu Glu Gln Asp Pro
    130                 135                 140

Ser Gly Ala Thr Thr Lys Ser Ala Met Leu Thr Asn Leu Ile Ile Phe
145                 150                 155                 160

Gly Pro Gly Pro Val Leu Asn Lys Asn Glu Val Arg Gly Ile Val Leu
                165                 170                 175

Arg Val Asp Asn Lys Asn Tyr Phe Pro Cys Arg Asp Gly Phe Gly Ser
            180                 185                 190

Ile Met Gln Met Ala Phe Cys Pro Glu Tyr Val Pro Thr Phe Asp Asn
        195                 200                 205

Val Ile Glu Asn Ile Thr Ser Leu Thr Ile Gly Lys Ser Lys Tyr Phe
    210                 215                 220

Gln Asp Pro Ala Leu Leu Leu Met His Glu Leu Ile His Val Leu His
225                 230                 235                 240

Gly Leu Tyr Gly Met Gln Val Ser Ser His Glu Ile Ile Pro Ser Lys
                245                 250                 255

Gln Glu Ile Tyr Met Gln His Thr Tyr Pro Ile Ser Ala Glu Glu Leu
            260                 265                 270

Phe Thr Phe Gly Gly Gln Asp Ala Asn Leu Ile Ser Ile Asp Ile Lys
        275                 280                 285

Asn Asp Leu Tyr Glu Lys Thr Leu Asn Asp Tyr Lys Ala Ile Ala Asn
    290                 295                 300

Lys Leu Ser Gln Val Thr Ser Cys Asn Asp Pro Asn Ile Asp Ile Asp
305                 310                 315                 320

Ser Tyr Lys Gln Ile Tyr Gln Gln Lys Tyr Gln Phe Asp Lys Asp Ser
                325                 330                 335

Asn Gly Gln Tyr Ile Val Asn Glu Asp Lys Phe Gln Ile Leu Tyr Asn
            340                 345                 350
```

```
Ser Ile Met Tyr Gly Phe Thr Glu Ile Glu Leu Gly Lys Lys Phe Asn
        355                 360                 365

Ile Lys Thr Arg Leu Ser Tyr Phe Ser Met Asn His Asp Pro Val Lys
    370                 375                 380

Ile Pro Asn Leu Leu Asp Asp Thr Ile Tyr Asn Asp Thr Glu Gly Phe
385                 390                 395                 400

Asn Ile Glu Ser Lys Asp Leu Lys Ser Glu Tyr Lys Gly Gln Asn Met
                405                 410                 415

Arg Val Asn Thr Asn Ala Phe Arg Asn Val Asp Gly Ser Gly Leu Val
            420                 425                 430

Ser Lys Leu Ile Gly Leu Cys Lys Lys Ile Ile Pro Pro Thr Asn Ile
        435                 440                 445

Arg Glu Asn Leu Tyr Asn Arg Thr Ala Ser Leu Thr Asp Leu Gly Gly
    450                 455                 460

Glu Leu Cys Ile Lys Ile Lys Asn Glu Asp Leu Thr Phe Ile Ala Glu
465                 470                 475                 480

Lys Asn Ser Phe Ser Glu Glu Pro Phe Gln Asp Glu Ile Val Ser Tyr
                485                 490                 495

Asn Thr Lys Asn Lys Pro Leu Asn Phe Asn Tyr Ser Leu Asp Lys Ile
            500                 505                 510

Ile Val Asp Tyr Asn Leu Gln Ser Lys Ile Thr Leu Pro Asn Asp Arg
        515                 520                 525

Thr Thr Pro Val Thr Lys Gly Ile Pro Tyr Ala Pro Glu Tyr Lys Ser
    530                 535                 540

Asn Ala Ala Ser Thr Ile Glu Ile His Asn Ile Asp Asp Asn Thr Ile
545                 550                 555                 560

Tyr Gln Tyr Leu Tyr Ala Gln Lys Ser Pro Thr Thr Leu Gln Arg Ile
                565                 570                 575

Thr Met Thr Asn Ser Val Asp Asp Ala Leu Ile Asn Ser Thr Lys Ile
            580                 585                 590

Tyr Ser Tyr Phe Pro Ser Val Ile Ser Lys Val Asn Gln Gly Ala Gln
        595                 600                 605

Gly Ile Leu Phe Leu Gln Trp Val Arg Asp Ile Ile Asp Asp Phe Thr
    610                 615                 620

Asn Glu Ser Ser Gln Lys Thr Thr Ile Asp Lys Ile Ser Asp Val Ser
625                 630                 635                 640

Thr Ile Val Pro Tyr Ile Gly Pro Ala Leu Asn Ile Val Lys Gln Gly
                645                 650                 655

Tyr Glu Gly Asn Phe Ile Gly Ala Leu Glu Thr Thr Gly Val Val Leu
            660                 665                 670

Leu Leu Glu Tyr Ile Pro Glu Ile Thr Leu Pro Val Ile Ala Ala Leu
        675                 680                 685

Ser Ile Ala Glu Ser Ser Thr Gln Lys Glu Lys Ile Ile Lys Thr Ile
    690                 695                 700

Asp Asn Phe Leu Glu Lys Arg Tyr Glu Lys Trp Ile Glu Val Tyr Lys
705                 710                 715                 720

Leu Val Lys Ala Lys Trp Leu Gly Thr Val Asn Thr Gln Phe Gln Lys
                725                 730                 735

Arg Ser Tyr Gln Met Tyr Arg Ser Leu Glu Tyr Gln Val Asp Ala Ile
            740                 745                 750

Lys Lys Ile Ile Asp Tyr Glu Tyr Lys Ile Tyr Ser Gly Pro Asp Lys
        755                 760                 765
```

```
Glu Gln Ile Ala Asp Glu Ile Asn Asn Leu Lys Asn Lys Leu Glu Glu
    770                 775                 780

Lys Ala Asn Lys Ala Met Ile Asn Ile Asn Ile Phe Met Arg Glu Ser
785                 790                 795                 800

Ser Arg Ser Phe Leu Val Asn Gln Met Ile Asn Glu Ala Lys Lys Gln
                805                 810                 815

Leu Leu Glu Phe Asp Thr Gln Ser Lys Asn Ile Leu Met Gln Tyr Ile
            820                 825                 830

Lys Ala Asn Ser Lys Phe Ile Gly Ile Thr Glu Leu Lys Lys Leu Glu
        835                 840                 845

Ser Lys Ile Asn Lys Val Phe Ser Thr Pro Ile Pro Phe Ser Tyr Ser
    850                 855                 860

Lys Asn Leu Asp Cys Trp Val Asp Asn Glu Glu Asp Ile Asp Val Ile
865                 870                 875                 880

Leu Lys Lys Ser Thr Ile Leu Asn Leu Asp Ile Asn Asn Asp Ile Ile
                885                 890                 895

Ser Asp Ile Ser Gly Phe Asn Ser Ser Val Ile Thr Tyr Pro Asp Ala
            900                 905                 910

Gln Leu Val Pro Gly Ile Asn Gly Lys Ala Ile His Leu Val Asn Asn
        915                 920                 925

Glu Ser Ser Glu Val Ile Val His Lys Ala Met Asp Ile Glu Tyr Asn
    930                 935                 940

Asp Met Phe Asn Asn Phe Thr Val Ser Phe Trp Leu Arg Val Pro Lys
945                 950                 955                 960

Val Ser Ala Ser His Leu Glu Gln Tyr Gly Thr Asn Glu Tyr Ser Ile
                965                 970                 975

Ile Ser Ser Met Lys Lys His Ser Leu Ser Ile Gly Ser Gly Trp Ser
            980                 985                 990

Val Ser Leu Lys Gly Asn Asn Leu  Ile Trp Thr Leu Lys  Asp Ser Ala
        995                 1000                1005

Gly Glu  Val Arg Gln Ile Thr  Phe Arg Asp Leu Pro  Asp Lys Phe
    1010                1015                1020

Asn Ala  Tyr Leu Ala Asn Lys  Trp Val Phe Ile Thr  Ile Thr Asn
    1025                1030                1035

Asp Arg  Leu Ser Ser Ala Asn  Leu Tyr Ile Asn Gly  Val Leu Met
    1040                1045                1050

Gly Ser  Ala Glu Ile Thr Gly  Leu Gly Ala Ile Arg  Glu Asp Asn
    1055                1060                1065

Asn Ile  Thr Leu Lys Leu Asp  Arg Cys Asn Asn Asn  Asn Gln Tyr
    1070                1075                1080

Val Ser  Ile Asp Lys Phe Arg  Ile Phe Cys Lys Ala  Leu Asn Pro
    1085                1090                1095

Lys Glu  Ile Glu Lys Leu Tyr  Thr Ser Tyr Leu Ser  Ile Thr Phe
    1100                1105                1110

Leu Arg  Asp Phe Trp Gly Asn  Pro Leu Arg Tyr Asp  Thr Glu Tyr
    1115                1120                1125

Tyr Leu  Ile Pro Val Ala Ser  Ser Ser Lys Asp Val  Gln Leu Lys
    1130                1135                1140

Asn Ile  Thr Asp Tyr Met Tyr  Leu Thr Asn Ala Pro  Ser Tyr Thr
    1145                1150                1155

Asn Gly  Lys Leu Asn Ile Tyr  Tyr Arg Arg Leu Tyr  Asn Gly Leu
    1160                1165                1170

Lys Phe  Ile Ile Lys Arg Tyr  Thr Pro Asn Asn Glu  Ile Asp Ser
```

```
    1175                1180                1185

Phe Val  Lys Ser Gly Asp Phe  Ile Lys Leu Tyr Val  Ser Tyr Asn
    1190                1195                1200

Asn Asn  Glu His Ile Val Gly  Tyr Pro Lys Asp Gly  Asn Ala Phe
    1205                1210                1215

Asn Asn  Leu Asp Arg Ile Leu  Arg Val Gly Tyr Asn  Ala Pro Gly
    1220                1225                1230

Ile Pro  Leu Tyr Lys Lys Met  Glu Ala Val Lys Leu  Arg Asp Leu
    1235                1240                1245

Lys Thr  Tyr Ser Val Gln Leu  Lys Leu Tyr Asp Asp  Lys Asn Ala
    1250                1255                1260

Ser Leu  Gly Leu Val Gly Thr  His Asn Gly Gln Ile  Gly Asn Asp
    1265                1270                1275

Pro Asn  Arg Asp Ile Leu Ile  Ala Ser Asn Trp Tyr  Phe Asn His
    1280                1285                1290

Leu Lys  Asp Lys Ile Leu Gly  Cys Asp Trp Tyr Phe  Val Pro Thr
    1295                1300                1305

Asp Glu  Gly Trp Thr Asn Asp
    1310                1315


<210> SEQ ID NO 17
<211> LENGTH: 1302
<212> TYPE: PRT
<213> ORGANISM: Artificial Sequence
<220> FEATURE:
<223> OTHER INFORMATION: poly-glycine modified neurotoxin polypeptide
<220> FEATURE:
<221> NAME/KEY: MISC_FEATURE
<222> LOCATION: (440)..(440)
<223> OTHER INFORMATION: "Gly" is poly-Glycine domain comprising up to
      300 glycine residues
<220> FEATURE:
<221> NAME/KEY: MISC_FEATURE
<222> LOCATION: (440)..(440)
<223> OTHER INFORMATION: additional "Cys" instead of poly-Glycine domain

<400> SEQUENCE: 17

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
```

-continued

```
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Gln
    210                 215                 220

Leu Ile Tyr Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Ala Gly Ala Gly Lys Ser Leu Val Pro Arg
        435                 440                 445

Gly Ser Ala Gly Ala Gly Ala Leu Asn Asp Leu Cys Ile Lys Val Asn
    450                 455                 460

Asn Trp Asp Leu Phe Phe Ser Pro Ser Glu Asp Asn Phe Thr Asn Asp
465                 470                 475                 480

Leu Asn Lys Gly Glu Glu Ile Thr Ser Asp Thr Asn Ile Glu Ala Ala
                485                 490                 495

Glu Glu Asn Ile Ser Leu Asp Leu Ile Gln Gln Tyr Tyr Leu Thr Phe
            500                 505                 510

Asn Phe Asp Asn Glu Pro Glu Asn Ile Ser Ile Glu Asn Leu Ser Ser
        515                 520                 525

Asp Ile Ile Gly Gln Leu Glu Leu Met Pro Asn Ile Glu Arg Phe Pro
    530                 535                 540

Asn Gly Lys Lys Tyr Glu Leu Asp Lys Tyr Thr Met Phe His Tyr Leu
545                 550                 555                 560

Arg Ala Gln Glu Phe Glu His Gly Lys Ser Arg Ile Ala Leu Thr Asn
                565                 570                 575

Ser Val Asn Glu Ala Leu Leu Asn Pro Ser Arg Val Tyr Thr Phe Phe
            580                 585                 590
```

```
Ser Ser Asp Tyr Val Lys Lys Val Asn Lys Ala Thr Glu Ala Ala Met
        595                 600                 605

Phe Leu Gly Trp Val Glu Gln Leu Val Tyr Asp Phe Thr Asp Glu Thr
    610                 615                 620

Ser Glu Val Ser Thr Thr Asp Lys Ile Ala Asp Ile Thr Ile Ile Ile
625                 630                 635                 640

Pro Tyr Ile Gly Pro Ala Leu Asn Ile Gly Asn Met Leu Tyr Lys Asp
                645                 650                 655

Asp Phe Val Gly Ala Leu Ile Phe Ser Gly Ala Val Ile Leu Leu Glu
            660                 665                 670

Phe Ile Pro Glu Ile Ala Ile Pro Val Leu Gly Thr Phe Ala Leu Val
        675                 680                 685

Ser Tyr Ile Ala Asn Lys Val Leu Thr Val Gln Thr Ile Asp Asn Ala
    690                 695                 700

Leu Ser Lys Arg Asn Glu Lys Trp Asp Glu Val Tyr Lys Tyr Ile Val
705                 710                 715                 720

Thr Asn Trp Leu Ala Lys Val Asn Thr Gln Ile Asp Leu Ile Arg Lys
                725                 730                 735

Lys Met Lys Glu Ala Leu Glu Asn Gln Ala Glu Ala Thr Lys Ala Ile
            740                 745                 750

Ile Asn Tyr Gln Tyr Asn Gln Tyr Thr Glu Glu Glu Lys Asn Asn Ile
        755                 760                 765

Asn Phe Asn Ile Asp Asp Leu Ser Ser Lys Leu Asn Glu Ser Ile Asn
    770                 775                 780

Lys Ala Met Ile Asn Ile Asn Lys Phe Leu Asn Gln Cys Ser Val Ser
785                 790                 795                 800

Tyr Leu Met Asn Ser Met Ile Pro Tyr Gly Val Lys Arg Leu Glu Asp
                805                 810                 815

Phe Asp Ala Ser Leu Lys Asp Ala Leu Leu Lys Tyr Ile Tyr Asp Asn
            820                 825                 830

Arg Gly Thr Leu Ile Gly Gln Val Asp Arg Leu Lys Asp Lys Val Asn
        835                 840                 845

Asn Thr Leu Ser Thr Asp Ile Pro Phe Gln Leu Ser Lys Tyr Val Asp
    850                 855                 860

Asn Gln Arg Leu Leu Ser Thr Phe Thr Glu Tyr Ile Lys Asn Ile Ile
865                 870                 875                 880

Asn Thr Ser Ile Leu Asn Leu Arg Tyr Glu Ser Asn His Leu Ile Asp
                885                 890                 895

Leu Ser Arg Tyr Ala Ser Lys Ile Asn Ile Gly Ser Lys Val Asn Phe
            900                 905                 910

Asp Pro Ile Asp Lys Asn Gln Ile Gln Leu Phe Asn Leu Glu Ser Ser
        915                 920                 925

Lys Ile Glu Val Ile Leu Lys Asn Ala Ile Val Tyr Asn Ser Met Tyr
    930                 935                 940

Glu Asn Phe Ser Thr Ser Phe Trp Ile Arg Ile Pro Lys Tyr Phe Asn
945                 950                 955                 960

Ser Ile Ser Leu Asn Asn Glu Tyr Thr Ile Ile Asn Cys Met Glu Asn
                965                 970                 975

Asn Ser Gly Trp Lys Val Ser Leu Asn Tyr Gly Glu Ile Ile Trp Thr
            980                 985                 990
```

```
Leu Gln Asp Thr Gln Glu Ile Lys  Gln Arg Val Val Phe  Lys Tyr Ser
        995                 1000                 1005

Gln Met  Ile Asn Ile Ser Asp  Tyr Ile Asn Arg Trp  Ile Phe Val
    1010                 1015                 1020

Thr Ile  Thr Asn Asn Arg Leu  Asn Asn Ser Lys Ile  Tyr Ile Asn
    1025                 1030                 1035

Gly Arg  Leu Ile Asp Gln Lys  Pro Ile Ser Asn Leu  Gly Asn Ile
    1040                 1045                 1050

His Ala  Ser Asn Asn Ile Met  Phe Lys Leu Asp Gly  Cys Arg Asp
    1055                 1060                 1065

Thr His  Arg Tyr Ile Trp Ile  Lys Tyr Phe Asn Leu  Phe Asp Lys
    1070                 1075                 1080

Glu Leu  Asn Glu Lys Glu Ile  Lys Asp Leu Tyr Asp  Asn Gln Ser
    1085                 1090                 1095

Asn Ser  Gly Ile Leu Lys Asp  Phe Trp Gly Asp Tyr  Leu Gln Tyr
    1100                 1105                 1110

Asp Lys  Pro Tyr Tyr Met Leu  Asn Leu Tyr Asp Pro  Asn Lys Tyr
    1115                 1120                 1125

Val Asp  Val Asn Asn Val Gly  Ile Arg Gly Tyr Met  Tyr Leu Lys
    1130                 1135                 1140

Gly Pro  Arg Gly Ser Val Met  Thr Thr Asn Ile Tyr  Leu Asn Ser
    1145                 1150                 1155

Ser Leu  Tyr Arg Gly Thr Lys  Phe Ile Ile Lys Lys  Tyr Ala Ser
    1160                 1165                 1170

Gly Asn  Lys Asp Asn Ile Val  Arg Asn Asn Asp Arg  Val Tyr Ile
    1175                 1180                 1185

Asn Val  Val Val Lys Asn Lys  Glu Tyr Arg Leu Ala  Thr Asn Ala
    1190                 1195                 1200

Ser Gln  Ala Gly Val Glu Lys  Ile Leu Ser Ala Leu  Glu Ile Pro
    1205                 1210                 1215

Asp Val  Gly Asn Leu Ser Gln  Val Val Val Met Lys  Ser Lys Asn
    1220                 1225                 1230

Asp Gln  Gly Ile Thr Asn Lys  Cys Lys Met Asn Leu  Gln Asp Asn
    1235                 1240                 1245

Asn Gly  Asn Asp Ile Gly Phe  Ile Gly Phe His Gln  Phe Asn Asn
    1250                 1255                 1260

Ile Ala  Lys Leu Val Ala Ser  Asn Trp Tyr Asn Arg  Gln Ile Glu
    1265                 1270                 1275

Arg Ser  Ser Arg Thr Leu Gly  Cys Ser Trp Glu Phe  Ile Pro Val
    1280                 1285                 1290

Asp Asp  Gly Trp Gly Glu Arg  Pro Leu
    1295                 1300


<210> SEQ ID NO 18
<211> LENGTH: 6
<212> TYPE: PRT
<213> ORGANISM: Artificial Sequence
<220> FEATURE:
<223> OTHER INFORMATION: thrombin proteolytic site

<400> SEQUENCE: 18

Leu Val Pro Arg Gly Ser
1               5
```